(12) United States Patent
Bissonnette et al.

(10) Patent No.: US 8,796,022 B2
(45) Date of Patent: Aug. 5, 2014

(54) GENERATION OF FUNCTIONAL BASAL FOREBRAIN CHOLINERGIC NEURONS FROM STEM CELLS

(75) Inventors: Christopher Bissonnette, Chicago, IL (US); John Kessler, Chicago, IL (US)

(73) Assignee: Northwestern University, Evanston, IL (US)

( * ) Notice: Subject to any disclaimer, the term of this patent is extended or adjusted under 35 U.S.C. 154(b) by 0 days.

(21) Appl. No.: 13/178,734

(22) Filed: Jul. 8, 2011

(65) Prior Publication Data
US 2012/0237484 A1 Sep. 20, 2012

Related U.S. Application Data

(60) Provisional application No. 61/362,555, filed on Jul. 8, 2010.

(51) Int. Cl.
| | |
|---|---|
| C12N 5/0793 | (2010.01) |
| C12N 15/85 | (2006.01) |
| A61P 25/28 | (2006.01) |
| A61K 35/30 | (2006.01) |
| C12N 5/0797 | (2010.01) |
| C12N 5/0735 | (2010.01) |

(52) U.S. Cl.
USPC .............. 435/377; 435/455; 424/93.7

(58) Field of Classification Search
CPC .. C12N 5/0606; C12N 5/0623; C12N 5/0619; C12N 2501/00; C12N 2501/10; C12N 2501/119; C12N 2501/113; C12N 2501/115; C12N 2501/155; C12N 2501/41; C12N 2501/60; C12N 15/63; C12N 15/85; A61K 38/18; A61K 38/1825; A61K 38/1875; A61K 38/1783; A61K 35/30
See application file for complete search history.

(56) References Cited

U.S. PATENT DOCUMENTS

2006/0134789 A1* 6/2006 Sugaya et al. ................ 435/455

OTHER PUBLICATIONS

Jennifer Ott Reilly, Irina D. Karavanova, Kevin P. Williams, Nagesh K. Mahanthappa, and Karen L. Allendoerfer, Cooperative Effects of Sonic Hedgehog and NGF on Basal Forebrain Cholinergic Neurons, 2002, Molecular and Cellular Neuroscience, vol. 19, pp. 88-96.*
Maya Schuldiner, Rachel Eiges, Amir Eden, Ofra Yanuka, Joseph Itskovitz-Eldor, Ronald S. Goldstein, Nissim Benvenisty, Induced neuronal differentiation of human embryonic stem cells, 2001, Brain Research, vol. 913, p. 210-5.*
Aletta C. Schnitzler, Ignacio Lopez-Coviella, Jan Krzysztof Blusztajn, Differential modulation of nerve growth factor receptor (p75) and cholinergic gene expression in purified p75-expressing and non-expressing basal forebrain neurons by BMP9, 2008, Brain Research, vol. 1246, pp. 19-28.*
Tod Gulick, Transfection Using DEAE-Dextran, 1997, Current Protocols in Neuroscience, A.1D.1-A.1D.10.*
Asbreuk et al., "The homeobox genes Lhx7 and Gbx1 are expressed in the basal forebrain cholinergic system," Neuroscience, 109(2): p. 287-298 (2002).

(Continued)

*Primary Examiner* — Blaine Lankford
*Assistant Examiner* — Trent R Clarke
(74) *Attorney, Agent, or Firm* — Casimir Jones S.C.

(57) ABSTRACT

The present invention provides method, compositions, and systems for generating basal forebrain cholinergic neurons (BFCNs) using FGF8, SHH, LXH8, GBX1, or vectors encoding these ligands, as well as using such BFCNs to treat neurological disorders such as Alzheimer's disease.

6 Claims, 23 Drawing Sheets

(56) References Cited

OTHER PUBLICATIONS

Disterhoft and Oh, "Pharmacological and molecular enhancement of learning in aging and Alzheimer's disease," J Physiol Paris, 99(2-3): p. 180-92 (2006).

Doering and Snyder, "Cholinergic expression by a neural stem cell line grafted to the adult medial septum/diagonal band complex," J Neurosci Res, 61(6), p. 597-604 (2000).

Fragkouli, et al., "Loss of forebrain cholinergic neurons and impairment in spatial learning and memory in LHX7-deficient mice," Eur j Neurosci, 21(11), p. 2923-38 (2005).

Genbank Accession No. NM_001001933; "*Homo sapiens* LIM homeobox 8 (LHX8), mRNA," http://www.ncbi.nlm.nih.gov/nuccore/NM_001001933, printed on Aug. 2, 2011.

Genbank Accession No. NM_001098834; "*Homo sapiens* gastrulation brain homeobox 1 (GBX1), mRNA," http://www.ncb.nlm.nih.gov/nuccore/NM_001098834, printed on Aug. 2, 2011.

Genbank Accession No. NM_130869; "*Mus musculus* Nobox oogenesis homeobox (Nobox), mRNA," http://www.ncbi.nlm.nih.gov/nuccore/NM_130869, printed on Aug. 2, 2011.

Grigoriou, M., et al., "Expression and regulation of Lhx6 and Lhx7, a novel subfamily of LIM homeodomain encoding genes, suggests a role in mammalian head development," Development, 125(11), p. 2063-74 (1998).

Mesulam, M., et al., "Cholinergic nucleus basalis tauopathy emerges early in the aging-MCI-AD continuum," Ann Neurol, 55 (6), p. 815-828 (2004).

Mori, T., et al., "The LIM homeobox gene, L3/Lhx8, is necessary for proper development of basal forebrain cholinergic neurons," Eur J Neurosci, 19(12), p. 3129-3141 (2004).

Mufson, E.J. et al., "Loss of basal forebrain P75(NTR) immunoreactivity in subjects with mild cognitive impairment and Alzheimer's disease," J Comp Neurol, 443 (2), p. 136-153 (2002).

Muir, J.L., "Acetylcholine, aging, and Alzheimer's disease," Pharmacol Biochem Behav, 56(4), 687-696 (1997).

Nobrega-Pereira, S., et al., "Postmitotic Nkx2-1 controls the migration of telencephalic interneurons by direct repression of guidance receptors," Neuron, 59(5), p. 733-745 (2008).

Power, A.E. et al., "Muscarinic cholingeric influences in memory consolidation," Neurobiol Learn Mem, 80 (3), p. 178-193 (2003).

Price, M., et al., "Regional expression of the homeobox gene Nkx-2.2 in the developing mammalian forebrain," Neuron, 8(2), p. 241-55 (1992).

Rhinn, et al., "Global and local mechanisms of forebrain and midbrain patterning," Curr Opin Neurobiol, 16(1), p. 5-12 (2006).

Schnitzler et al., "Purification and culture of nerve growth factor receptor (p75)-expressing basal forebrain cholinergic neurons," Nat Protoc, 3(1), p. 34-40 (2008).

Sussel, L., et al., "Loss of Nkx2.1 homeobox gene function results in a ventral to dorsal molecular respecification within the basal telencephalon: evidence for a transformation of the pallidum into the striatum," Development, 126(15), p. 3359-70 (1999).

Zhao, Y., et al., "Isolated cleft palate in mice with a targeted mutation of the LIM homeoboxgene LhxB," Proc Natl Acad Sci USA, 96(26), p. 15002-15006 (1999).

Zhao, Y., et al., "The LIM-homeobox gene Lhx8 is required for the development of many cholinergic neurons in the mouse forebrain," Proc Natl Acad Sci USA, 100(15), p. 9005-10 (2003).

\* cited by examiner

```
ATGAGTCCGGAGGGCGACACCCCCAGCCCGCCTGCTCGCCCGCCCCCTCCTTATGAGAGAG
AGGGAGCGCGGCGCCGGAGCCACACTGCGCCGAGCCCGCGCCCCGCCGCCACCTCGGCCCG
GGAGCCAGGGAGCGAGCCCTGCGTGTCCGCGCGGGGCGCCCGAGCCGCGGGGCGCACGGA
GGCGCCCAGAGAGGAGCGCCCCGGGGCGGCCGCAGCTCCGAACAAGATGCAGCGGGCCGG
AGGCGGTAGCGCCCTGGGGGCAACGGCGGGGGCGGCGGCGGGGGCCCGGGCACTGCCTT
CTCCATCGACTCCCTAATCGGGCCGCCGCCGCCGCGCTCCGGCCACTTGCTGTACACCGGC
TACCCCATGTTCATGCCCTACCGGCCGCTCGTGCTGCCGCAGGCGCTGGCCCCTGCGCCGC
TGCCCGCTGGCCTCCCGCCCCTCGCCCCGCTAGCCTCTTTCGCCGGCCGCCTTACCAACAC
CTTCTGCGCGGGGCTGGGTCAGGCTGTGCCCTCGATGGTGGCGCTGACCACCGCGCTGCC
CAGCTTCGCGGAGCCGCCCGACGCTTTCTACGGGCCCCAGGAGCTCGCCGCCGCCGCTGCC
GCCGCCGCCGCCACTGCCGCCCGAAACAACCCCGAGCCAGGCGGCCGACGCCCAGAGGGT
GGGCTGGAAGCTGATGAGCTGCTGCCGGCCCGGGAGAAAGTGGCAGAGCCCCCACCACCT
CCGCCTCCGCACTTCTCAGAGACTTTTCCAAGTCTGCCCGCAGAGGGGAAGGTGTACAGC
TCAGATGAGGAGAAGCTGGAGGCATCAGCAGGAGACCCAGCAGGCAGCGAACAGGAGGA
AGAGGGCTCAGGCGGTGACAGCGAGGATGACGGTTTCCTGGACAGTTCTGCAGGGGGCCC
AGGGGCTCTTCTGGGACCTAAACCGAAGCTAAAGGGAAGCCTGGGGACTGGAGCTGAGG
AGGGGGCACCGGTGACAGCAGGGGTCACAGCTCCTGGGGGGAAAAGCCGACGGCGCCGCA
CAGCATTTACCAGCGAGCAGCTTTTGGAATTGGAGAAGGAATTTCATTGCAAGAAATAC
CTGAGCTTGACAGAGCGCTCTCAGATCGCCCACGCCCTCAAGCTCAGTGAGGTGCAGGTC
AAGATCTGGTTTCAGAATCGACGGGCCAAGTGGAAGCGCATCAAAGCTGGCAATGTGAG
CAGCCGTTCTGGGGAGCCCGTAAGAAACCCCAAGATTGTTGTCCCCATACCTGTGCATGT
CAACAGGTTTGCTGTGCGGAGCCAGCACCAACAAATGGAGCAGGGGGCCCGGCCCTGA
```

GENERATION OF FUNCTIONAL BASAL FOREBRAIN CHOLINERGIC NEURONS FROM STEM CELLS

CROSS-REFERENCE TO RELATED APPLICATIONS

The present application claims the benefit of U.S. Provisional Patent Application No. 61/362,555, filed Jul. 8, 2010, which is incorporated by reference in its entirety.

STATEMENT REGARDING GOVERNMENT FUNDING

This invention was made with government support under grant number 5 P50 NS054287 awarded by the National Institutes of Health. The government has certain rights in the invention.

FIELD OF THE INVENTION

The present invention provides method, compositions, and systems for generating basal forebrain cholinergic neurons (BFCNs) using FGF8, SHH, LHX8, GBX1, or vectors encoding these ligands, as well as using such BFCNs to treat neurological disorders such as Alzheimer's disease.

BACKGROUND

The basal forebrain cholinergic system is the predominant source of cortical cholinergic input and is comprised of cholinergic projection neurons travelling from the basal telencephalon through the neocortex to the hippocampus, olfactory system, cortical mantle, and amygdala. Alzheimer's disease-related tauopathies arise earliest in cholinergic neurons of the basal forebrain and loss of these neurons parallels cognitive decline (1-4). Human lesion (5-7) and MRI (8) studies have demonstrated the role of BFCN in memory function, while studies in monkeys, rats and mice using a specific BFCN immunotoxin have further demonstrated the role of these cells in memory function (9-12), hippocampal neurogenesis, and the survival of new neurons (13-15). Additionally, numerous animal models have demonstrated the necessity of BFCN for functional plasticity of the motor cortex after training (16) or damage (17), and also throughout the visual (18) and auditory (19) cortices, data which can be partially replicated with anticholinergic drugs in humans (20). Being of such import in Alzheimer's disease, memory formation, and cortical plasticity, the derivation of BFCN from human stem cells could be of great potential therapeutic benefit as it might allow the repopulation of BFCN after loss or damage.

SUMMARY OF THE INVENTION

The present invention provides method, compositions, and systems for generating basal forebrain cholinergic neurons (BFCNs) using FGF8, SHH, LHX8, GBX1, or vectors encode these ligands, as well as using such BFCNs to treat neurological disorders such as Alzheimer's disease or Parkinson's disease.

In some embodiments, the present invention provides methods of generating basal forebrain cholinergic neurons (BFCNs) comprising: treating neural progenitor cells with at least one ligand, or an expression vector that expresses the ligand, wherein the ligand is selected from the group consisting of: FGF8, a biologically active fragment or variant of FGF8; a FGF8 small molecule mimetic; sonic hedgehog (SHH), or a biologically active fragment or variant of SHH, or a SHH mimetic; LHX8 or a biologically active fragment or variant thereof (or a LHX8 mimetic), GBX1 or a biologically active fragment or variant thereof (or GBX1 mimetic); wherein the treating generates BFCNs. In certain embodiments, the neural progenitor cells are contacted with some or all of the above recited ligands. For example, in certain embodiments, the neural progenitor cells are contacted with both LHX8 and GBX1. In other embodiments, the neural progenitor cells are contacted with SHH and/or FGF8 and both LHX8 and GBX1, or vectors encoding some or all of the recited ligands.

In particular embodiments, the methods further comprise generating the neural progenitor cells by treating embryonic stem cells with retinoic acid. In certain embodiments, the ligand is a human ligand (e.g., human SHH or FGF8). In other embodiments, neural progenitor cells are human neural progenitor cells. In other embodiments, the methods further comprise treating the neutral progenitor cells with BMP9. In additional embodiments, the methods further comprise transfecting the neural progenitors with vectors that cause overexpression of Lhx8 (e.g., human accession number NM_001001933, or mouse accession number NM_130869), or biologically active fragment or variant thereof, and Gbx1 (e.g., human accession number NM_001098834) or a biologically active fragment or variant thereof.

In certain embodiments, the present invention provides methods of generating basal forebrain cholinergic neurons (BFCNs) comprising: transfecting neural progenitor cells with vectors that cause overexpression of Lhx8 and Gbx1, wherein the transfecting generates BFCNs. In some embodiments, the methods further comprise generating the neural progenitor cells by treating embryonic stem cells with retinoic acid. In further embodiments, the neural progenitor cells are human neural progenitor cells. In other embodiments, the methods further comprise treating the neural progenitor cells with at least one ligand selected from the group consisting of: FGF8, a biologically active fragment or variant of FGF8; a FGF8 small molecule mimetic; sonic hedgehog (SHH), or a biologically active fragment or variant of SHH, or a SHH small molecule mimetic.

In particular embodiments, the present invention provides methods of treating a patient with a neurological disorder comprising: implanting an isolated population of BFCN's into the brain area of a patient with a neurological disorder. In certain embodiments, the BFCN's are generated according to the methods described herein. In further embodiments, the neurological disorder is Alzheimer's disease or related disease. In certain embodiments, the neurological disorder is Parkinson's disease.

In some embodiments, the present invention provides system and kits comprising: a) neural progenitor cells, and b) at least one ligand selected from the group consisting of: FGF8, a biologically active fragment or variant of FGF8; a mimetic of FGF8 (e.g., a small molecule mimetic of FGF8), sonic hedgehog (SHH), or a biologically active fragment or variant of SHH, or a mimetic of SHH (e.g., small molecule mimetic).

In certain embodiments, the present invention provides system and kits comprising: a) neural progenitor cells, and b) at least one expression vector configured for expressing a ligand selected from the group consisting of: FGF8, a biologically active fragment or variant of FGF8; a mimetic of FGF8 (e.g., a small molecule mimetic of FGF8), sonic hedgehog (SI-1H), or a biologically active fragment or variant of SHH, or a mimetic of SHH (e.g., small molecule mimetic).

In some embodiments, the present invention provides systems comprising: a) neural progenitor cells, and b) at least one ligand, or at least one expression vector encoding the ligand, wherein the ligand is selected from the group consisting of: FGF8, a biologically active fragment or variant of FGF8; sonic hedgehog (SHH), or a biologically active fragment or variant of SHH; LHX8, or a biologically active fragment or variant of LHX8; and GBX1, or a biologically active fragment or variant of GBX1.

DETAILED DESCRIPTION OF THE INVENTION

Figure 1:
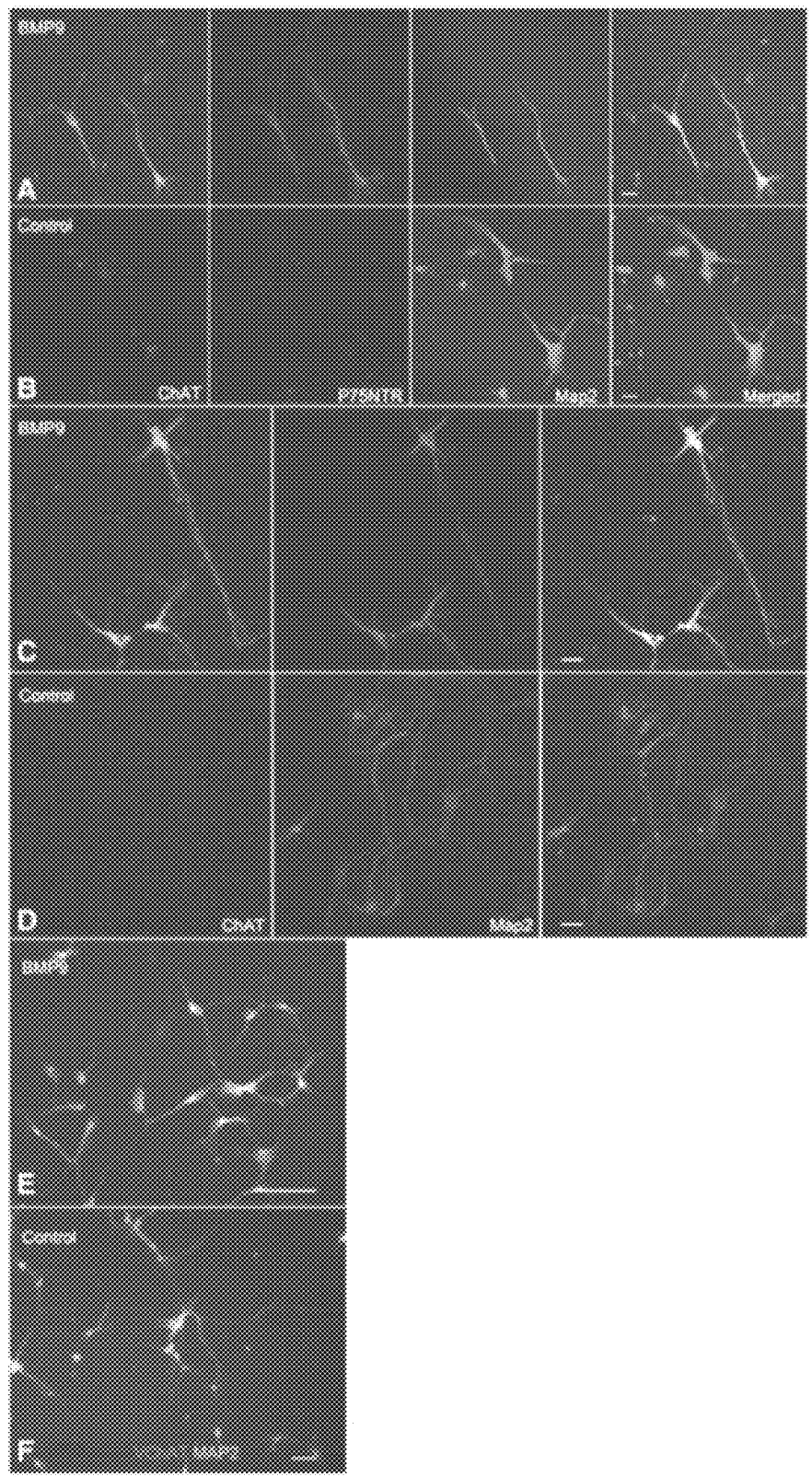
FIG. 1 shows generation of BFCN through BMP9 treatment. a,b: Confocal microscopy demonstrates that cells generated through BMP9 treatment of FGF8/SSH pretreated neural progenitors express ChAT, p75, and MAP2 and have a projection neuron morphology, while control neurons are only MAP2 positive. c,d: Confocal microscopy of equivalent cells stained only for ChAT and MAP2 show the same BMP9 response and long ChAT+, MAP2-axons. All scale bars=20 uM. e: qRT-PCR analysis shows 12-40 fold increases of RNA levels for markers characteristic of the BFCN. Bars are standard error, N=4. All increases were significant by ANOVA (p values: *<0.0001, =0.0014, *<0.0001,****<0.0001). Data are from four replicate experiments; error bars show s.e.m. fig: BMP9-mediated ChAT immunopositivity is associated with expression of the vesicular acetylcholine transporter (VChaT). Lower magnification analysis of fields of neurons stained for VChAT. Scale bars=100 uM. Data in a-d,f-g are from five replicate experiments, data in e is from 4 replicate experiments; error bars show s.e.m.
Figure 1:
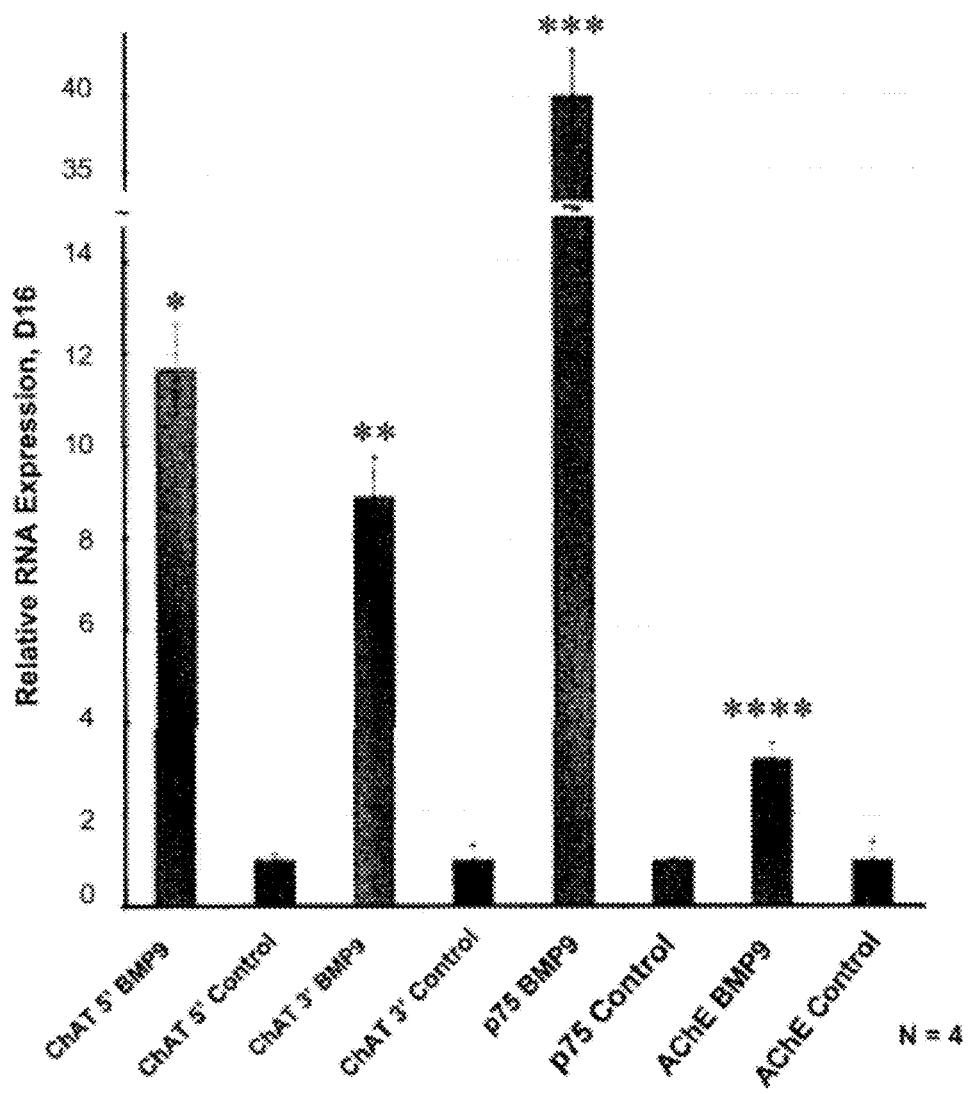

The present invention provides method, compositions, and systems for generating basal forebrain cholinergic neurons (BFCNs) using FGF8, SHH, LHX8, GBX1, or vectors encoding these ligands, as well as using such BFCNs to treat neurological disorders such as Alzheimer's disease.

An early substantial loss of basal forebrain cholinergic neurons (BFCN) is a constant feature of Alzheimer's disease and is associated with deficits in spatial learning and memory. The ability to selectively control the differentiation of human embryonic stem cells (hESC) into BFCN would be a significant step towards a cell replacement therapy. Work conducted during development of embodiments of the present invention demonstrated a method for the derivation of a predominantly pure population of BFCN from hESC cells using diffusible ligands present in the forebrain at developmentally relevant time periods. Overexpression of two relevant human transcription factors (Lhx8 and Gbx1) in hESC-derived neural progenitors also generates BFCN. These neurons express only those markers characteristic of BFCN, generate action potentials, and form functional cholinergic synapses in ex vivo murine hippocampal slice cultures. siRNA-mediated knockdown of the transcription factors blocks BFCN generation by the diffusible ligands, clearly demonstrating the factors both necessary and sufficient for the controlled derivation of this neuronal population.

Although 14 distinct regional subpopulations of BFCN exist in murine cortex, the group arising from the median ganglionic eminence (MGE) is the largest and best characterized (21, 22); derivation of a human population of such cells was thus the focus of the Example below. Several proteins are characteristic of BFCN in vivo and in vitro. Choline acetyltransferase (ChAT), which catalyzes the formation of acetylcholine, is expressed by cholinergic neurons of both the basal forebrain and the motor system. In the cortex, TrkA, the high-affinity nerve growth factor receptor, is expressed by BFCN from development through adulthood (23), and is necessary for NGF-mediated survival of these neurons (24). The low-affinity neurotrophin receptor (p75NTR, p75), is also expressed by more than 95% of ChAT-positive cells in the basal forebrain (25). BFCN should also express acetylcholinesterase (AChE), but not NADPH diaphorase, somatostatin, or HB-9, which are specific to cortical, amygdalar, and motor cholinergic neuronal subpopulations.

Although BFCN are neurotrophin responsive, these neurons are still present in murine knockouts of TrkA (26), or p75 (27, 28), demonstrating that neither these receptors nor NGF (29) are required for BFCN lineage commitment. However bone morphogenetic protein-9 (BMP9, Growth and Differentiation Factor 2 (GDF2)), a member of the transforming growth factor-β (TGF-β) superfamily of signaling factors (30), is transiently expressed in vivo in the septum during the period of BFCN development, and treatment of mouse septal cultures with BMP9 increases expression of cholinergic markers. Injection of BMP9 into E14 and E16 mouse ventricles increases levels of acetylcholine detectable in the forebrain (31), and BMP9 induces the transcriptome of BFCN in cultured murine septal progenitors (32). The effects of BMP9 on cholinergic neurogenesis are both spatially and temporally limited, having minimal effects outside of the E14-16 septum (31).

Several transcription factors have been implicated in the differentiation of MGE-derived BFCN. Lhx8, a LIM-family homeodomain transcription factor, is expressed in the developing MGE (33); although sequentially related to Lhx6 (34), and with overlapping domains of expression, Lhx8-expressing cells become cholinergic neurons while Lhx6-expressing cells become GABAergic interneurons (35, 36). Lhx8-positive cells which become BFCN also express Gbx1 (35). Different murine Lhx8 knockout lines (37-39), have slightly different phenotypes, but all have distinct and specific reductions in BFCN with minimal effects on other neuronal subtypes. Transgenic cells expressing dysfunctional Lhx8 neither multiplied, died, nor differentiated, and continued to induce Gbx1 mRNA, demonstrating both Lhx8's involvement in differentiation of committed progenitors into a cholinergic phenotype without altering proliferation or survival, and Gbx1's independent induction and insufficiency for BFCN formation (38, 40). Nkx2.1, necessary for encoding the regional identity of the M GE, is expressed during development in all cells derived from this region (41). Nkx2.1 knockout animals lack BFCN (42) and all other populations generated in or migrating through the MGE.

EXAMPLES

Example 1

Figure 4:
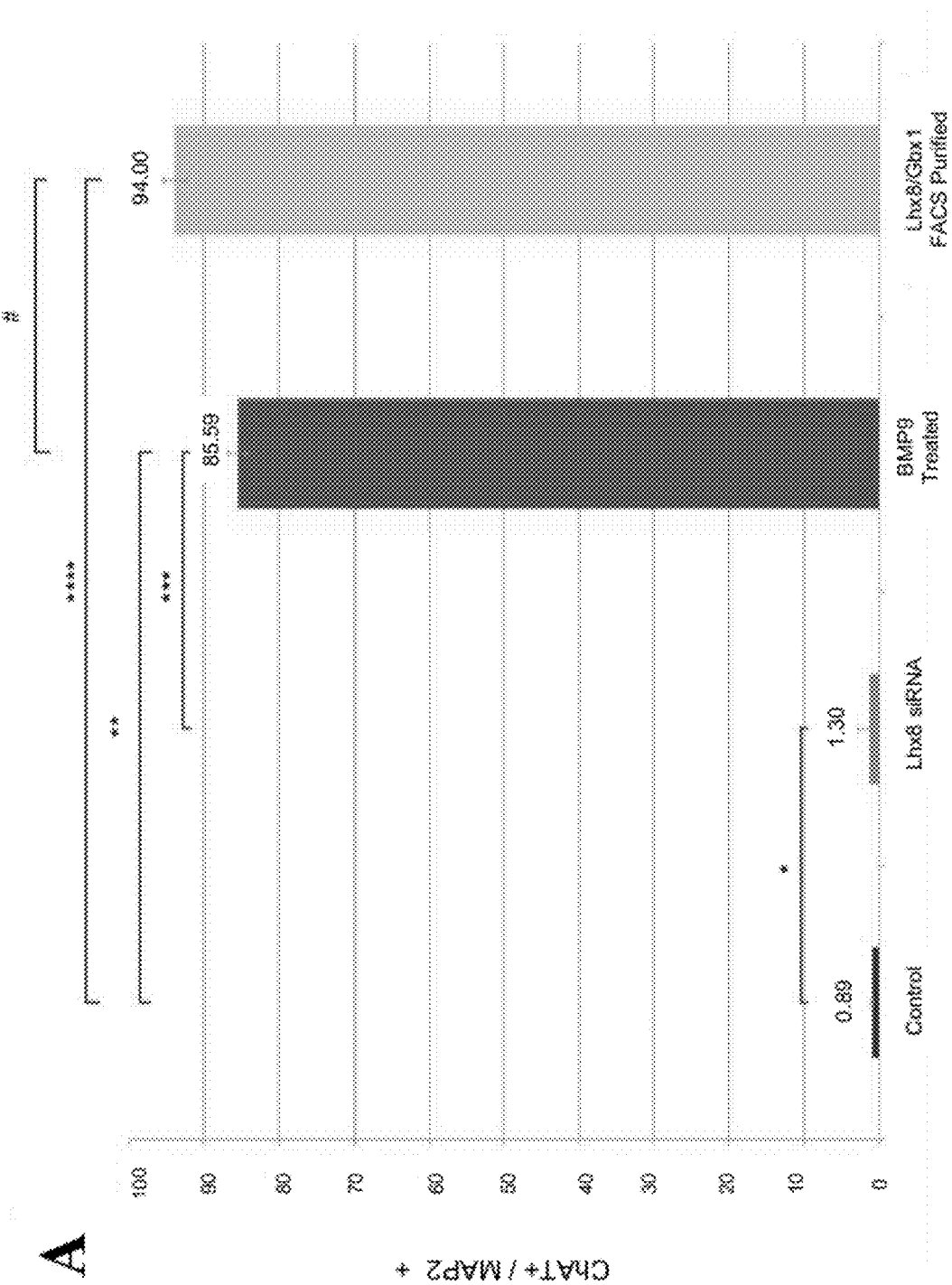
FIG. 4 shows quantification of neuronal differentiation into BFCN. a: A high percentage of neurons from the FACS-purified (94.00±1.53%) or BMP9-treated (85.59±1.31%) populations are ChAT immunopositive, while control (0.89±0.24%) and LhxB siRNA-treated (1.26±1.33%) populations fail to express ChAT. All populations are significantly different by Mann-Whitney U Test (p values: *=0.035, <0.001, *=0.001,****=0.006) except BMP9 vs Nucleofected (#, p=0.066). N=4,700 control, 2,565 siRNA, 2,582 BMP9, or 1,718 nucleofected cells from 4 (control, BMP9 and nucleofected) or 3 (siRNA) replicate cultures. Error bars show s.e.m. b: Representative ChAT immunohistochemistry demonstrates the clear distinction of ChAT immunopositivity between positive and negative cells. Scale bar=20 uM.
Figure 4:
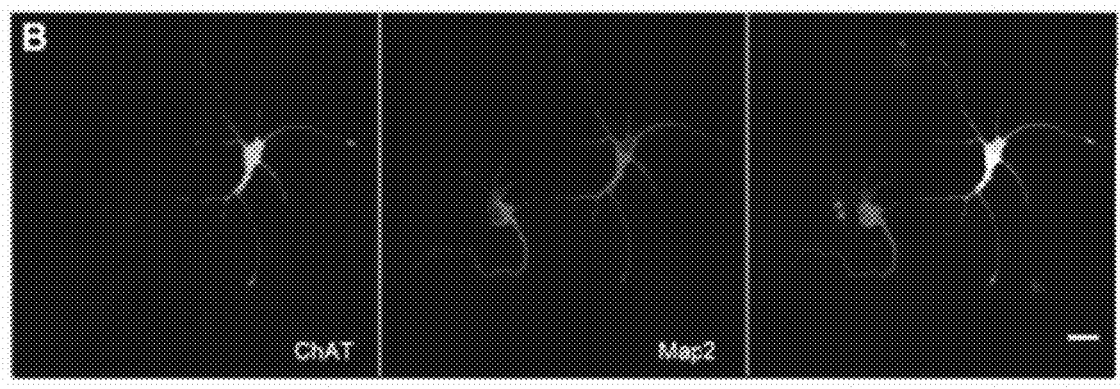
Figure 7:
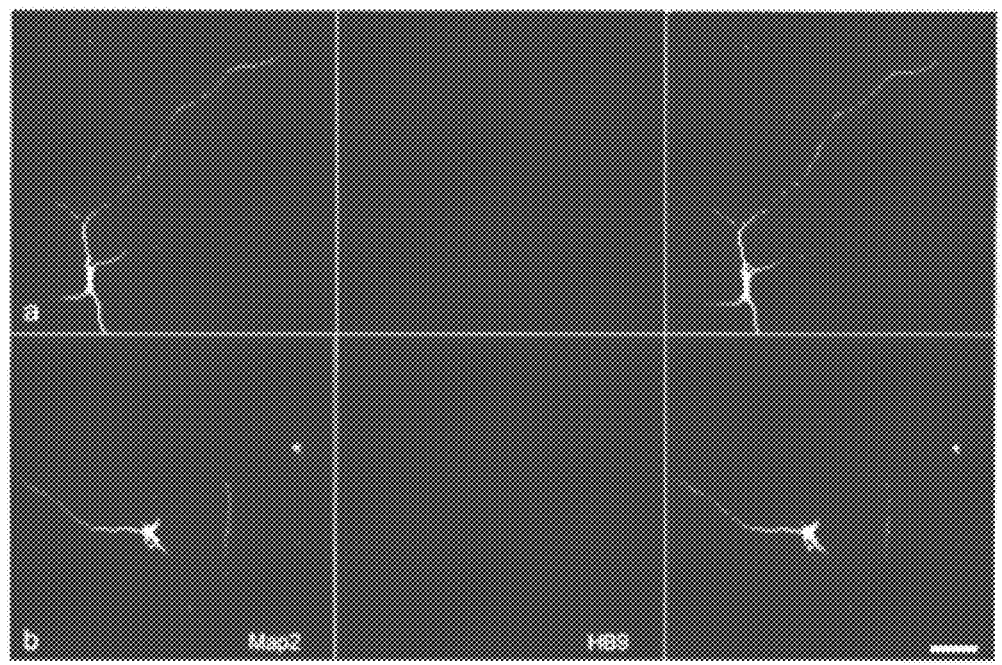
FIG. 7 shows HB9 Immunohistochemistry. a,b: At maximum 594 nM laser intensity on a confocal microscope, presumptive BFCN generated through BMP9 treatment are not HB9 (HLXB9) immunopositive, indicating that they are not cholinergic motor neurons. Scale bar=20 uM.
Figure 8:
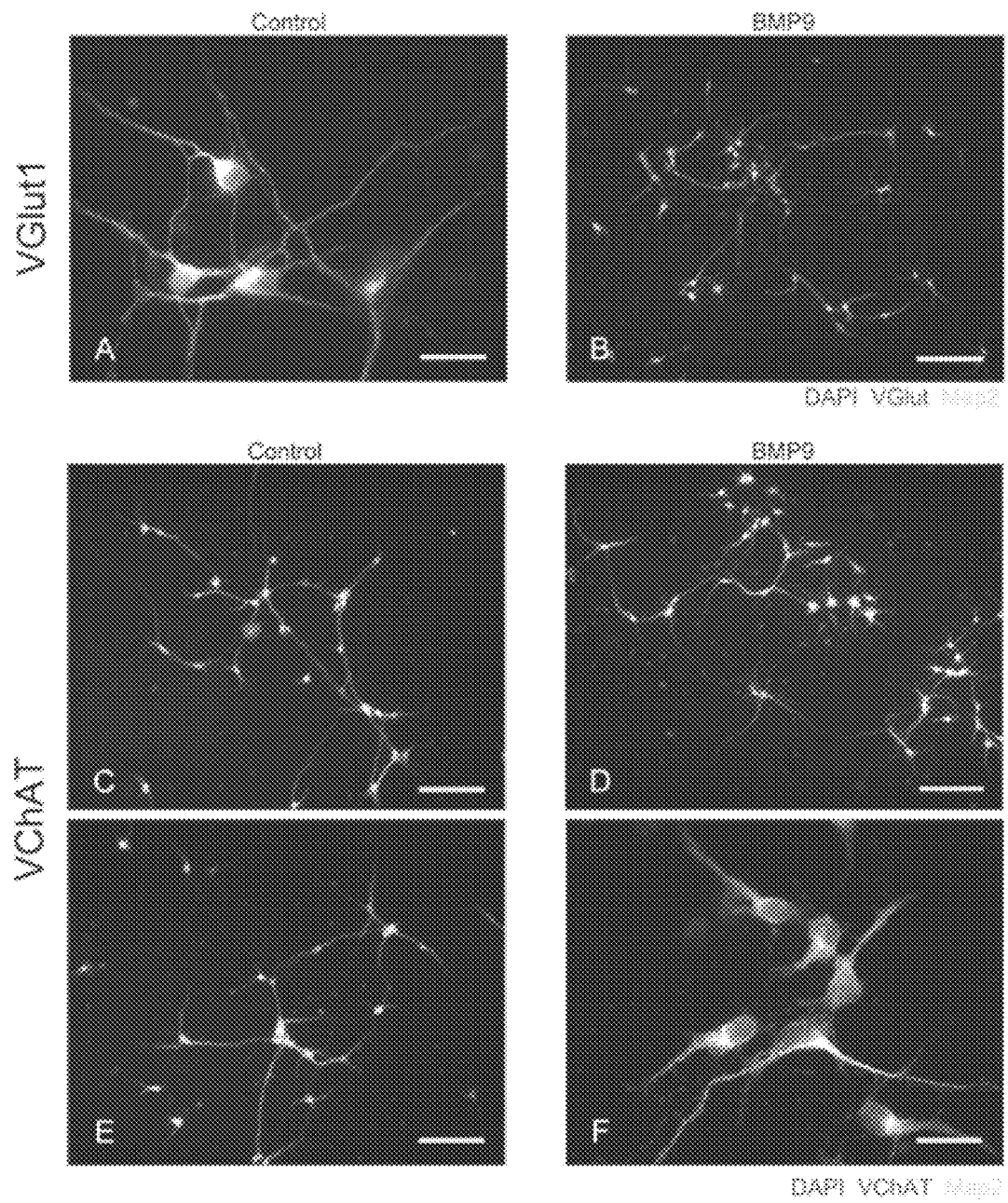
FIG. 8 shows BMP9 activity changes hNSC-derived neurons from a glutamatergic to cholinergic phenotype. Control neurons express high levels of VGlut1 (a) but low levels of VChAT (c,e), while 72 hours of 10 ng ml-1 BMP9 treatment after SHH/FGF8 pretreatment results in an opposite phenotype, with low levels of Vglut1 (b) and high expression of VChAT (d,f). These data suggest that the control neurons generated in these experiments default to a glutamatergic phenotype, and BMP9 is able to alter this default lineage commitment towards a cholinergic phenotype. Scale bars: a,f=20~M, b-e=100 uM
Figure 9:
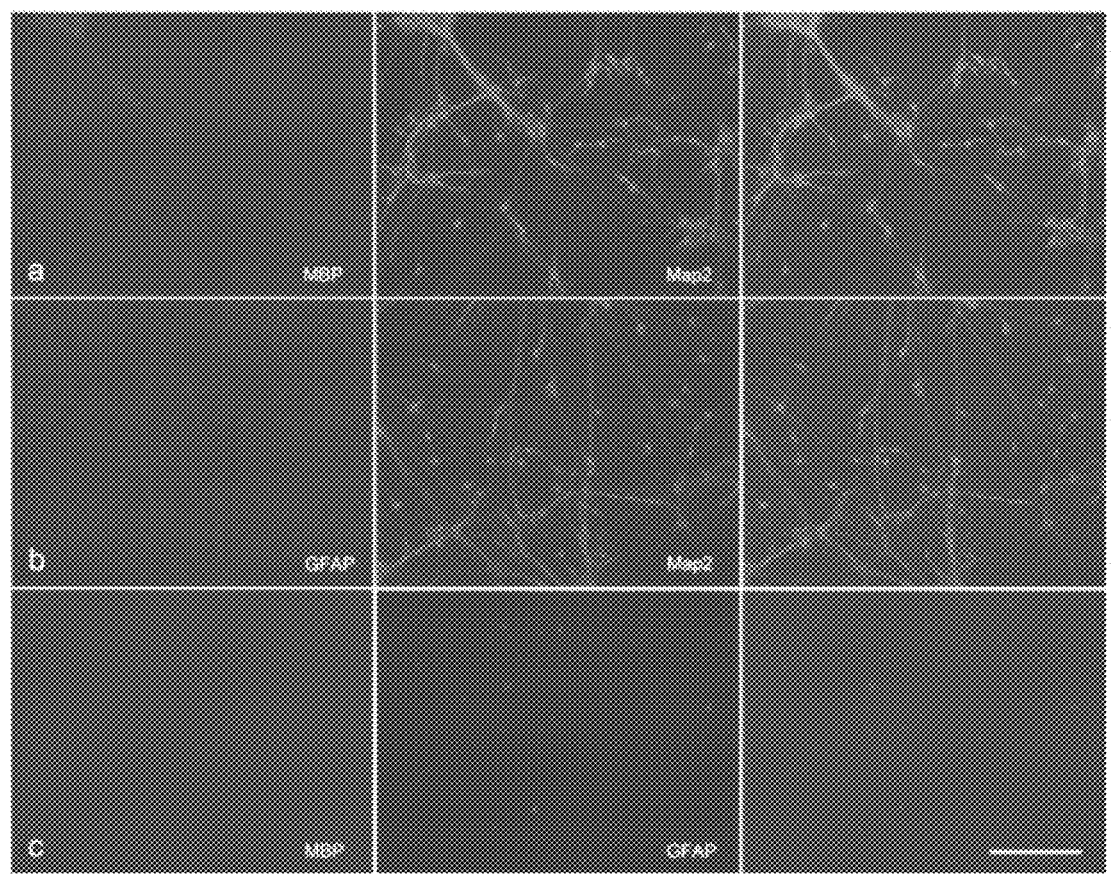
FIG. 9 shows culture conditions utilized only support neuronal growth. Combinatorial staining for MBP and MAP2 (a), GFAP and MAP2 (b), or GFAP and MBP (c) show that the cultures generated through the BMP9 treatment paradigm contain only neurons after 16 days in these media conditions, and are free of oligodendroglial (MBP) or astroglial (GFAP) cells. Scale bar=100 uM.
Figure 10:
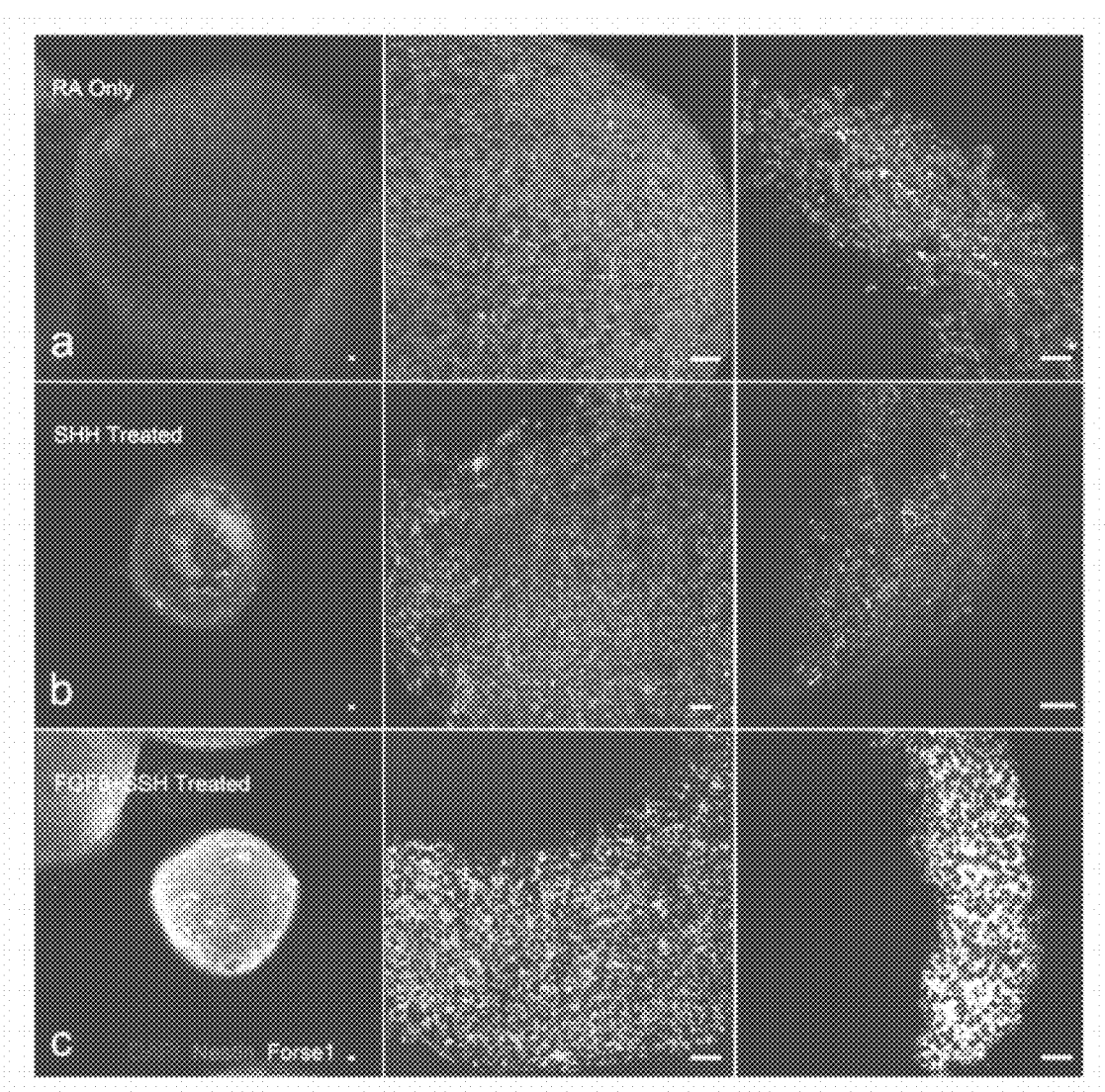
FIG. 10 shows FORSE1 immunohistochemistry demonstrates the generation of forebrain progenitor cells. FORSE1 is an antibody specific to forebrain progenitor cells which binds to the Lex phosphacan, a brain-specific chondroitin sulfate proteoglycan. a: Neurospheres generated using the culture system are almost uniformly nestin positive (red immunofluorescence), but the control retinoic acid-derived cells do not express FORSE1 (green immunofluorescence), which correlates with their inability to be driven towards a BFCN lineage. b: Cells pretreated for 72 hours in 200 ng ml$^{-1}$ SHH alone show a small increase in FORSE1 staining, and some ability to be made into BFCN (Not Shown). c: Neurospheres pretreated for 72 hours in 100 ng ml-i FGF8 and 200 ng ml$^{-1}$ SHH show a marked increase in both FORSE1 expression and the ability to become BFCN (FIGS. 1,2,4). Scale bars=20 uM.
Figure 11B:
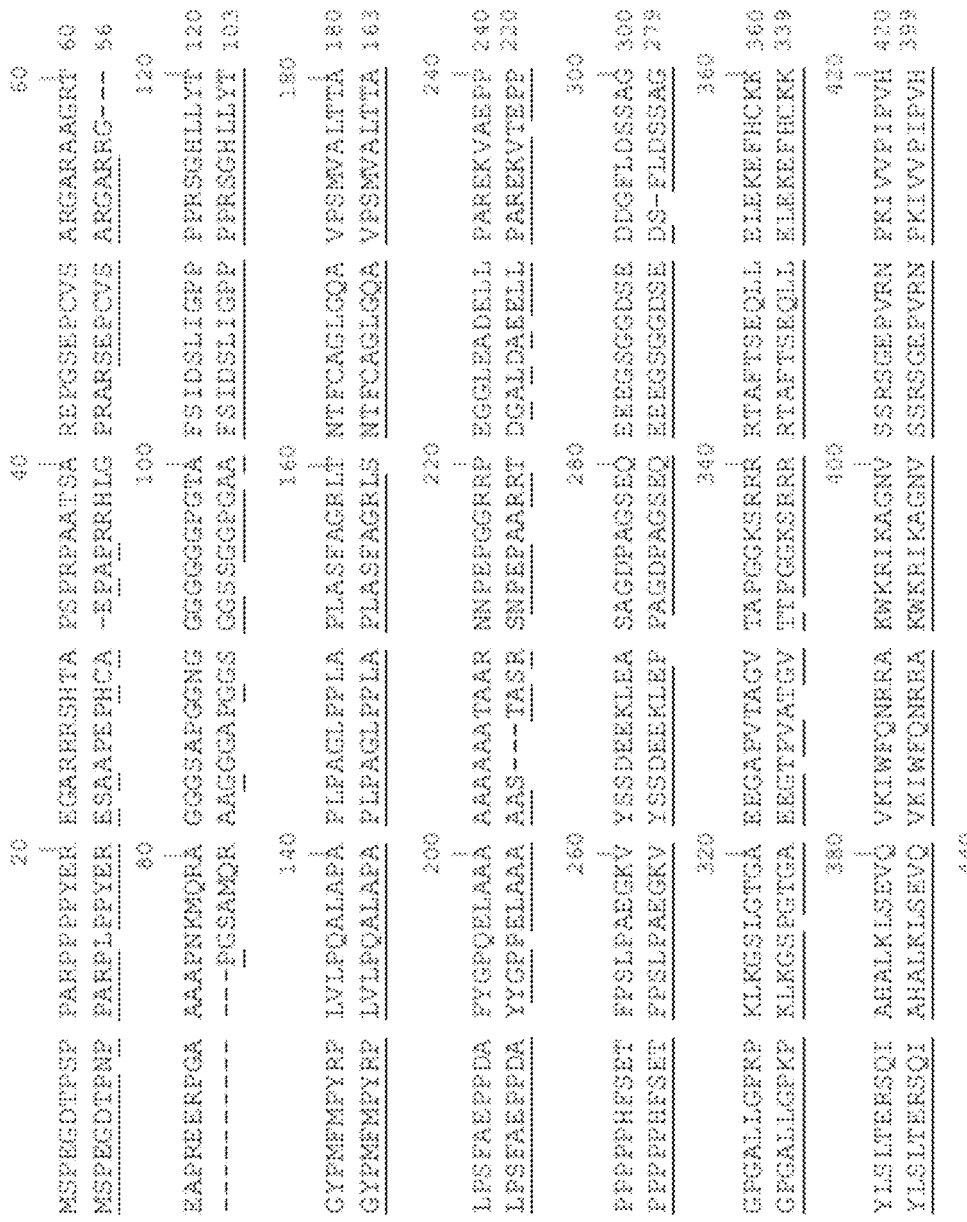
FIG. 11 shows the sequence of full length Gbx1 determined through RACE experiments. a: Nucleotide sequence of the novel human Gbx1 sequence (SEQ ID NO:1). b: The human (upper sequence; SEQ ID NO:2) and murine (lower sequence; SEQ ID NO:3) Gbx1 proteins have a high level of homology.
Figure 12:
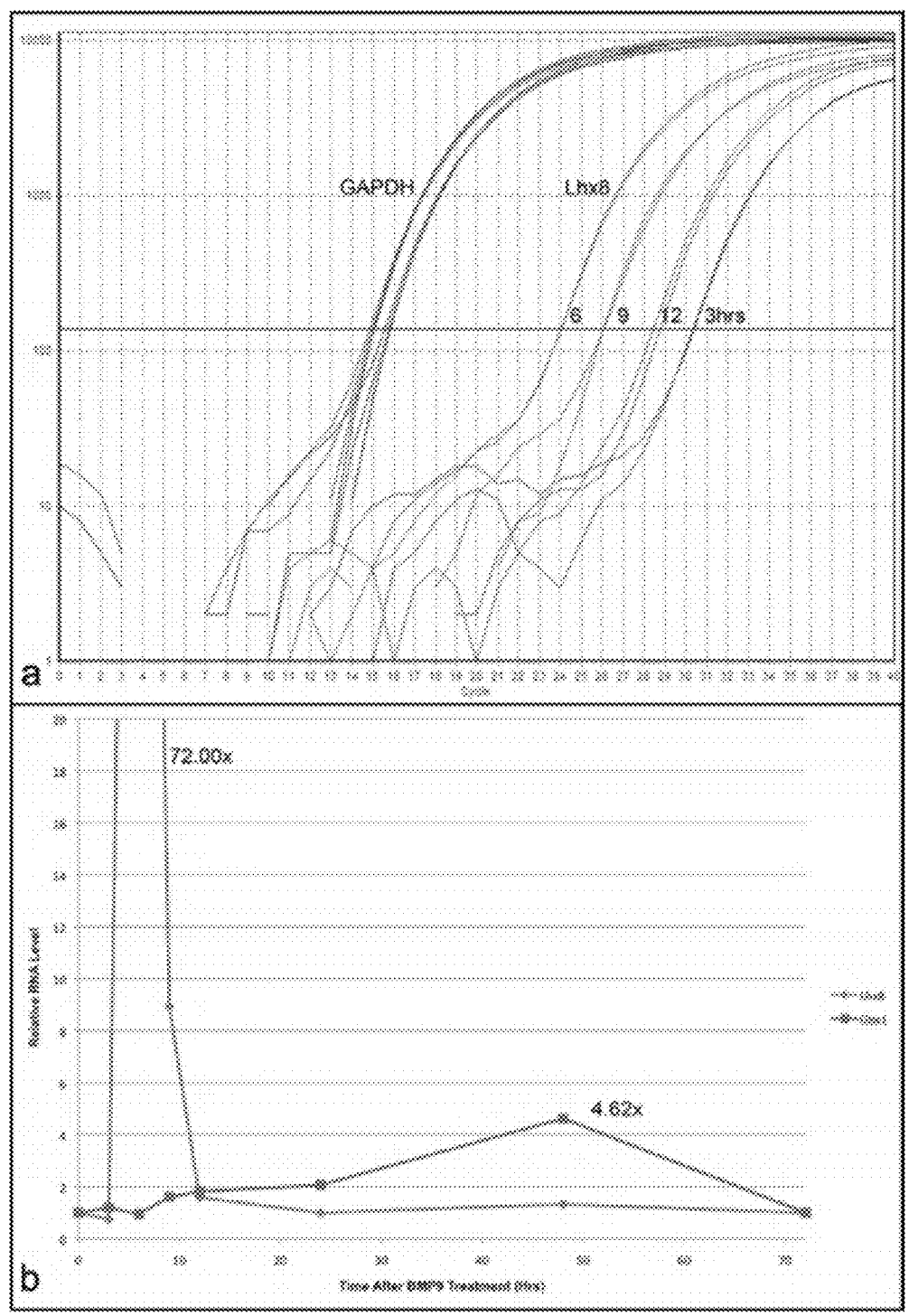
FIG. 12 shows the transcription factor induction following BMP9 treatment. a: Representative qRT-PCR curves showing the distinct upregulation of LhxB expression between 3 and 12 hours after 10 ng ml$^{-1}$ BMP9 treatment of human neurospheres. b: Time course of transcription factor response to BMP9 treatment. LhxB levels increased to 72× baseline at 6 hours, while Gbx1 levels gradually increased to 4.62× baseline over 48 hours. Related factors, such as Lhx6 and Isl1 were unchanged following BMP9 treatment.

Controlled Generation of Functional Basal Forebrain Cholinergic Neurons from Human Embryonic Stem Cells This example describes the generation of functional basal forebrain cholinergic neurons from human embryonic stem cells.
Results
Generation of Basal Forebrain Cholinergic Neurons Using Diffusible Ligands Methods were initially developed to differentiate hESCs into BFCN through treatment with diffusible ligands known to be expressed in the developing murine MGE. hESC-derived neural progenitors (hNSCs) were first generated using retinoic acid and published protocols (43). As FGF8 and sonic hedgehog (SHH) are necessary for patterning the developing neural tube and specification of the primordial forebrain (44), and together induce the transcriptome of the MGE while inhibiting LGE-specific factors (45), pretreatment with SHH and FGF8 was used to differentiate hNSCs towards a forebrain progenitor fate. FGF8/SHH preprogrammed hNSCs were then dissociated and treated with BMP9. qRT-PCR analysis of these neurons at D16 (FIG. 1e) shows a large, significant increase in the expression of markers for the BFCN lineage, including ChAT, p75, TrkA, and AChE, while markers for other populations of cholinergic neurons, such as somatostatin and nitric oxide synthase, are expressed at levels below control neuronal cultures. TuJ1 levels remain unchanged, indicating that BMP9/FGF8/SHH treatment alters lineage selection within progenitors already committed to a neural fate. Immunostaining at D19 for ChAT or p75 shows a vast increase in numbers of Map2+/marker+ cells, (immunocytochemistry FIG. 1a; counts FIG. 4a) with 85.59±1.31% of cells becoming ChAT positive neurons with a projection neuron morphology, while 9.24±1.19% become ChAT negative cells with an interneuron morphology (N=5 replicate cultures; 2,582 cells). There is no HB9 (HLXB9) immunopositivity, indicating that these cholinergic neurons are not motor neurons (FIG. 7a,b). Control neurospheres, derived in parallel but neither pretreated with FGF8/SHH nor treated with BMP9, yielded 0.89±0.24% cholinergic neurons (N=4 cultures; 4,700 cells) (FIG. 1b,c), and expressed markers consistent with glutamatergic neurons (FIG. 8). Neither control nor BMP9 treated cultures contained cells immunopositive for markers of an astroglial (GFAP) or oligodendroglial (MBP) lineage (FIG. 9a-c) at D16. BMP9-derived neuronal axon growth and RNA expression were NGF-responsive, indicating their expression of TrkA. Direct treatment of hESC (instead of the FGF8/SHH restricted hNSC) with BMP9 did not generate neurons; without SHH/FGF8 pretreatment neurospheres generate progenitors which fail to become BFCN after BMP9 treatment. Pretreating with SHH alone before BMP9 treatment yielded neurons with BFCN-like RNA expression patterns, but with much lower neuronal survival than when FGF8 was added. These data indicate that a temporally precise regime of neural restriction, followed by pretreatment with forebrain-specifying factors, followed by exposure to a factor expressed in the MGE during BFCN generation is able to generate a population of neurons significantly enhanced for markers of the BFCN lineage. Although this diffusible ligand treatment greatly increases the percentage of BFCN generated from hESC cells (85%), derivation of a pure population of any single cell type using extracellular signaling molecules may potentially not be possible due to heterogeneity of both hESC and hESC-derived neural progenitors. Although staining for FORSE1, an immunohistochemical marker of forebrain progenitors (46), increases greatly after FGF8/SHH pretreatment (FIG. 10), expression is not uniform, and progeny from these neurospheres vary depending on the hESC passage number and the duration in culture between neurosphere generation and dissociation.
Generation of Basal Forebrain Cholinergic Neurons Through Controlled Gene Expression Because hNSC had variable, highly timing-dependant responses to BMP9 treatment (only 85% BFCN) it was wondered if an increased purity of BFCN could be generated through controlled expression of specific human genes, potentially bypassing differences in hNSC expression of receptors or downstream signaling components. Based on murine embryology, the transcription factors Lhx8 and Gbx1 were chosen for further study. Since no complete human Gbx1 sequence has been published, the full-length human sequence, with an ORF encoding 439 amino acids (FIG. 11), was derived through RACE experiments using a human 13-week fetal brain mRNA library. Involvement of these genes as downstream effectors of the BMP9 signaling cascade was confirmed through treating either control or FGF8/SHH-pretreated neurospheres with BMP9 and analyzing the time courses of individual transcription factor responses (FIG. 12). Lhx8 transcripts increased 72-fold at 6 hours following BMP9 treatment and remained elevated for 12 hours before decreasing. Gbx1 had a delayed 4.62-fold increase at 48 hrs after treatment, while factors with high sequence homology (Lhx-6) or related to other neuronal populations (Is)etl), were unaffected by BMP9 treatment. Control (non-FGF8/SHH pretreated) neurospheres had negligible changes in transcription factor expression following BMP9 treatment, mirroring their inability to generate cholinergic neurons. Although not detected in intact neurospheres, Nkx2.1 RNA expression was transiently detected 12 hours after neurosphere dissociation, indicating that, as expected, these neurons are derived from an Nkx2.1-expressing progenitor lineage.

Figure 2:
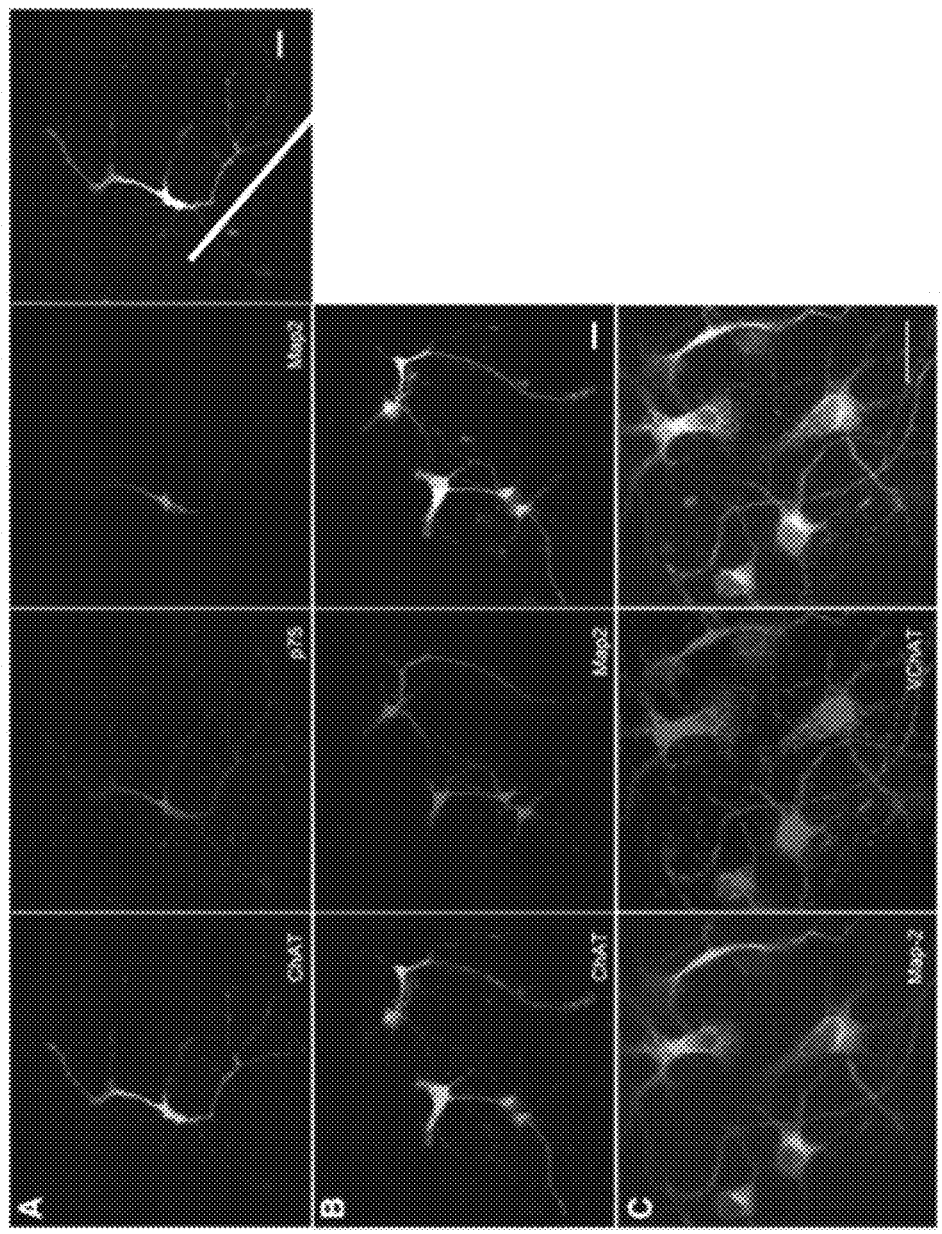
FIG. 2 shows generation of BFCN through transcription factor overexpression. a: Confocal analysis of FACS-purified neurons shows strong expression of ChAT, p75, and MAP2. b: Confocal microscopy shows FACS-purified neurons immunostained only for ChAT and MAP2. c: FACS-purified neurons shown at higher power contain large numbers of vesicles positive for VChAT. All scale bars=20 uM. d: qRT-PCR analysis shows large increases in ChAT and p75 RNA transcript levels. Bars show s.e.m., N=4. Both increases were shown to be significant by ANOVA (p values: *=0.0002, **=0.0031).
Figure 2:
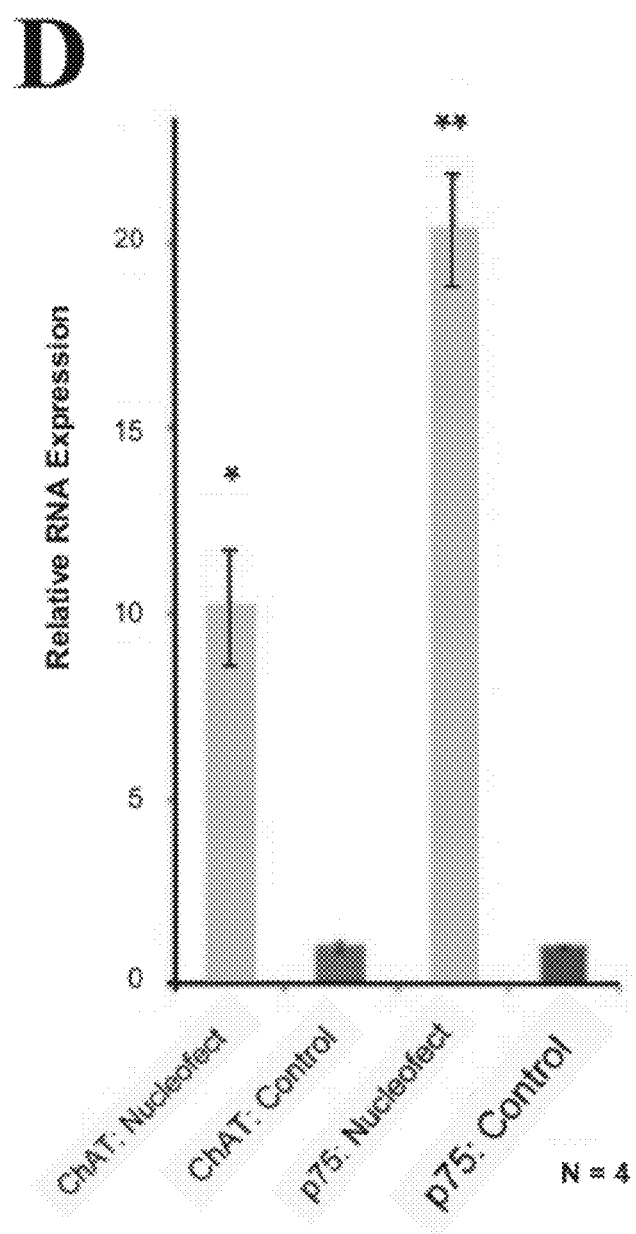
Figure 13:
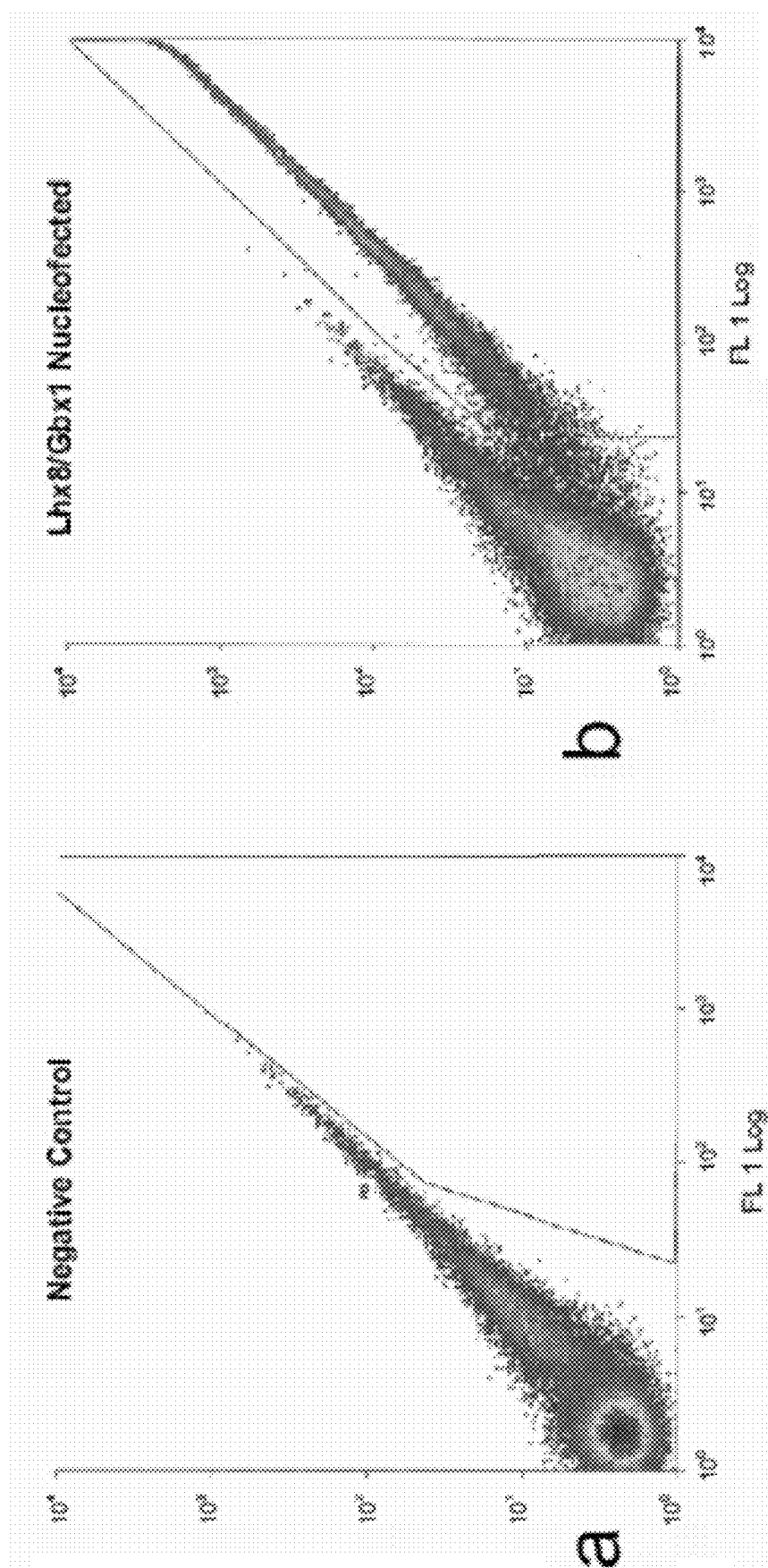
FIG. 13 shows representative FACS data. After gating to remove debris and doublets, neurons were FACS-purified based on GFP expression; only cells with expression levels markedly above the negative control were kept while minimally-expressing cells were discarded.

Since Lhx8 and Gbx1 are specifically upregulated by BMP9 treatment of hNSCs, a technique was developed for nucleofection-based overexpression of these factors with a constitutively-active eGFP (enhanced-Green Fluorescent Protein) in FGF8/SHH-pretreated hNSCs, allowing for FACS-based purification of overexpressing cells. Expression of each factor individually in neural progenitors resulted in neurons with reproducible morphologies and RNA expression patterns, but without the BFCN phenotype. FGF8/SHH-treated forebrain progenitors were nucleofected and grown without BMP9. For RNA experiments, populations of cells were used without FACS-purification. Although only ~40% of cells were successfully nucleofected in each group (FIG. 13), this was sufficient to significantly increase expression of markers for the BFCN lineage (FIG. 2); these data were confirmed with FACS-purified neurons. The nucleofected cells were FACS purified 48 hours after nucleofection and then cultured for 19 days. Immunostaining for ChAT showed that 94.00±1.53% of cells became cholinergic neurons with long projecting axons, while the remainder became neurons without ChAT expression or with an interneuron morphology (N=3 cultures, 1,718 cells). Confocal analysis confirmed that the ChAT immunopositivity was entirely contained within the neuronal cytoplasm (FIG. 8a-c, FIG. 10b). Dual immunostaining for ChAT/p75 demonstrated that these cells are positive for both markers, whereas control neurons are 18.67±0.88% p75 positive. These RNA and immunohistochemical data show that the FACS-purified transiently Lhx8/Gbx1-overexpressing cells from SHH/FGF8 pretreated neural progenitors, when grown for 19 days in culture, are a highly purified population of human neurons expressing only those markers characteristic of the BFCN.

BMP9 and Lhx8/Gbx1 Overexpression Function Through One Pathway

Figure 3:
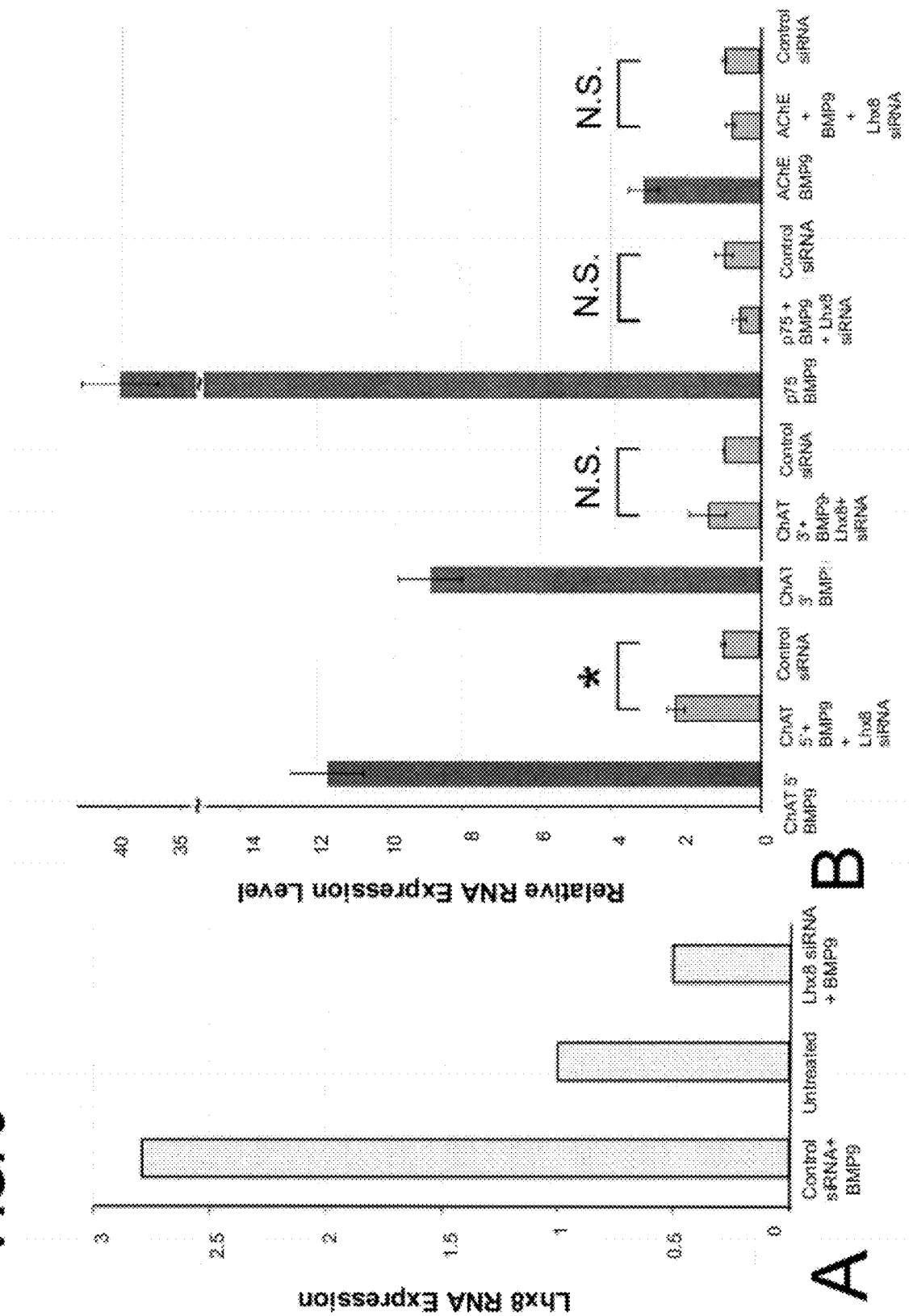
FIG. 3 shows LhxB siRNA blocks BMP9 effects on BFCN differentiation. a: LhxB siRNA nucleofection blocks the BMP9 mediated increase in LhxB levels, causing a reduction in LhxB transcript to levels below basal expression when compared to scrambled siRNA nucleofection after BMP9 treatment of dissociated and plated neural progenitors. b: qRT-PCR analysis indicates that LhxB siRNA inhibits the BMP9-mediated BFCN differentiation of human neural progenitors, with only a 2-fold but still significant increase in levels of ChAT mRNA (p*=0.0225) after the siRNA treatment. c: Neurons generated from LhxB siRNA-expressing neural progenitors fail to become ChAT immunopositive. Scale bar=20 uM. Data in b-c are from three replicate experiments; error bars show s.e.m.
Figure 3:
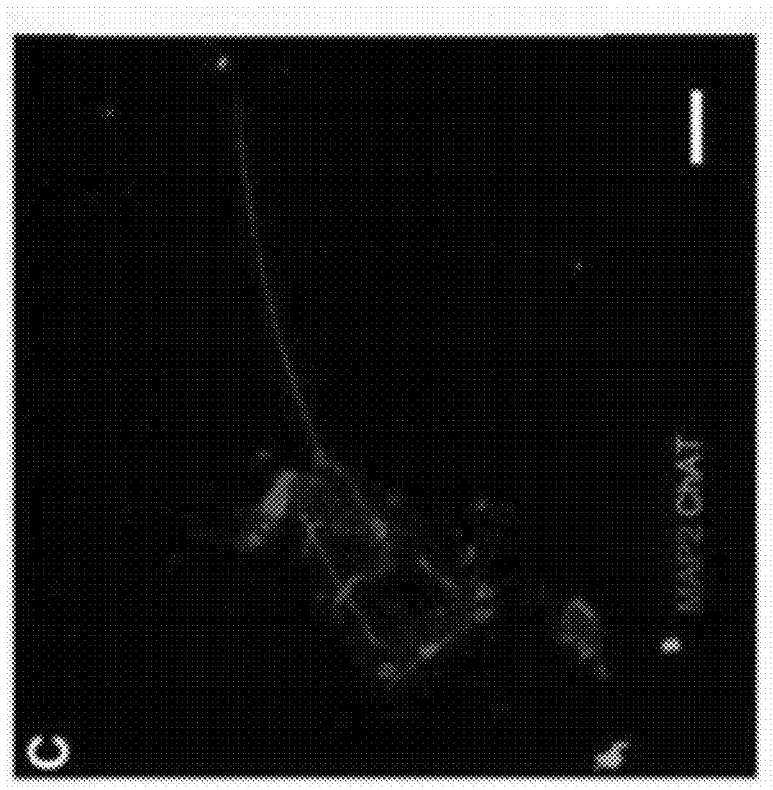

Although these experiments demonstrate that the transcription factors Lhx8 and Gbx1 respond to BMP9 signaling after FGF8/SHH pretreatment and are able to drive progenitors towards a BFCN phenotype, it remained to be shown that the transcription factors were the downstream mediators of BMP9 signaling along a common pathway. To determine this, an siRNA-mediated knockdown of Lhx8 was performed on FGF8/SHH pretreated neural progenitors. Simultaneously with the BMP9 treatment paradigm. Co-nucleofection of the Lhx8 siRNA with a fluorescently-labeled scrambled siRNA indicated that over 900/0 of surviving cells were successfully treated with the siRNA. The siRNA blocked the BMP9 mediated upregulation of Lhx8 levels, reducing Lhx8 levels below basal expression (FIG. 3a). qRT-PCR analysis at D16 after Lhx8 knockdown demonstrates greatly reduced BFCN marker expression compared to equivalent BMP9 treated cells without siRNA (FIG. 3b), and immunohistochemistry showed an equivalent reduction to 1.26±1.33% of MAP2-positive neurons expressing ChAT (immunocytochemistry FIG. 3c, counts FIG. 4a) (N=3 cultures, 2,565 cells). The ability of Lhx8 knockdown to block the effects of BMP9 treatment indicates that it is a necessary downstream effector of the BMP9-mediated signaling cascade in FGFS/SHH pretreated neural progenitors, and demonstrates that the BMP9 treatment and the Lhx8/Gbx1 overexpression studies function through the same pathway. That the Lhx8-specific knockdown blocks the effects of BMP9 further supports the conclusion that the ChAT+, p75+, Map2+ cells generated by both the small molecule and transcription factor treatments are BFCN since this is the only neuronal population specifically lost after null mutation of Lhx8 (37-39).

ChAT Staining Correlates with Enzymatically Functional ChAT

The functionality of the ChAT detected by immunohistochemistry was confirmed through direct detection of acetylcholine. The cytoplasm of neurons from both derivation methods had markedly increased ACh levels: 5.11±0.66 ngACh/ugProtein for BMP9 treatment and 6.94±3.06 ngACh/ugProtein from nucleofections vs. 0.83±0.02 ngACh/ugProtein for control neurons (N=3 replicate cultures/condition); as expected, Lhx8 siRNA expression reduced acetylcholine levels towards basal levels—1.79±0.16 ngACh/ugProtein. These data confirm that neuronal ChAT immunopositivity correlates to functional ChAT enzymatic activity.

Neurons Engraft in Mouse Ex Vivo Slice Cultures

Figure 5:
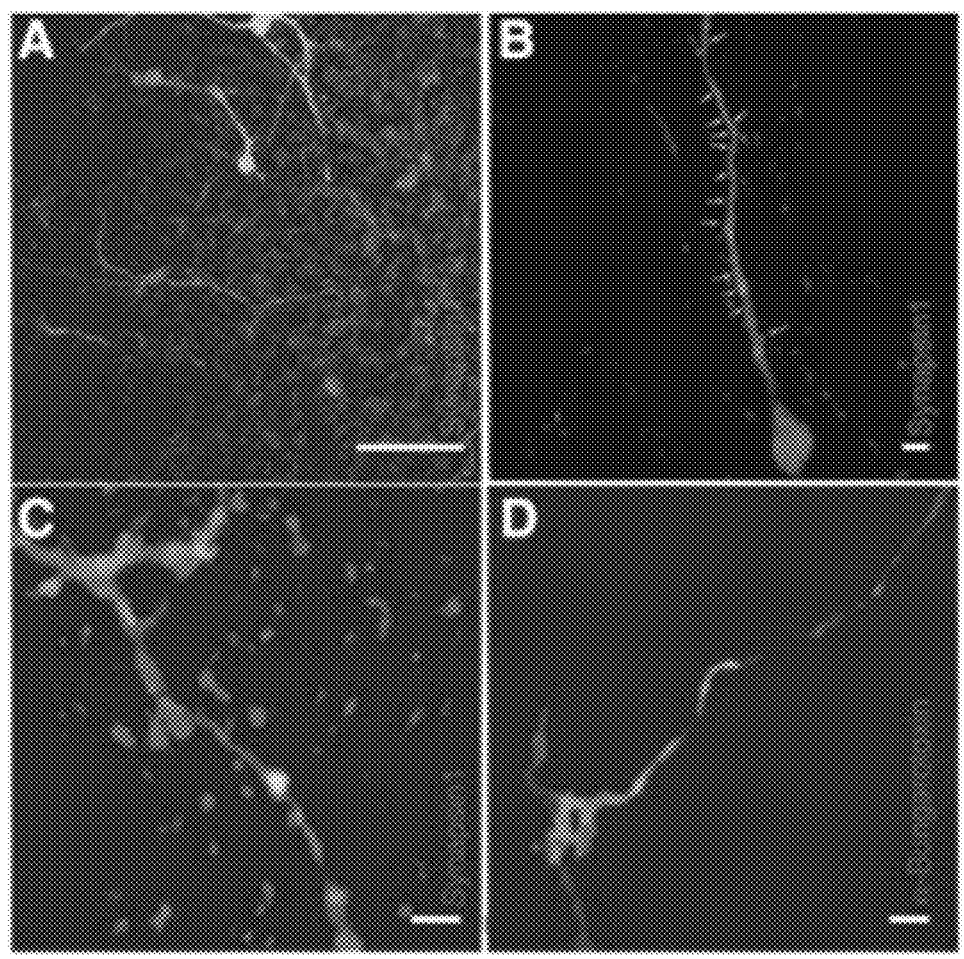
FIG. 5 shows immunohistochemical evidence for, and characterization of, functional synaptic transmission after engraftment of FACS-purified neurons into murine ex vivo hippocampal slice cultures. a: FACS-purified neuronal populations stably engraft in mouse hippocampal ex vivo slice cultures and project long networks of axons. All green fluorescence in FIG. 5 is the eGFP expression from the adenovirally-labeled FACS-purified LhxB/Gbx1 transiently overexpressing neurons. Scale bar=50 uM. b: Murine presynaptic terminals (synapsin1, red channel) line the axons of the engrafted cells, giving immunohistochemical verification of the electrophysiologically detected synaptic inputs to these cells. Scale bar=5 uM. c: Transcription factor-generated basal forebrain cholinergic neurons contain presynaptic terminals (synapsin1, red channel) within their axons, indicating that they are generating synapses with other neurons.
Figure 14:
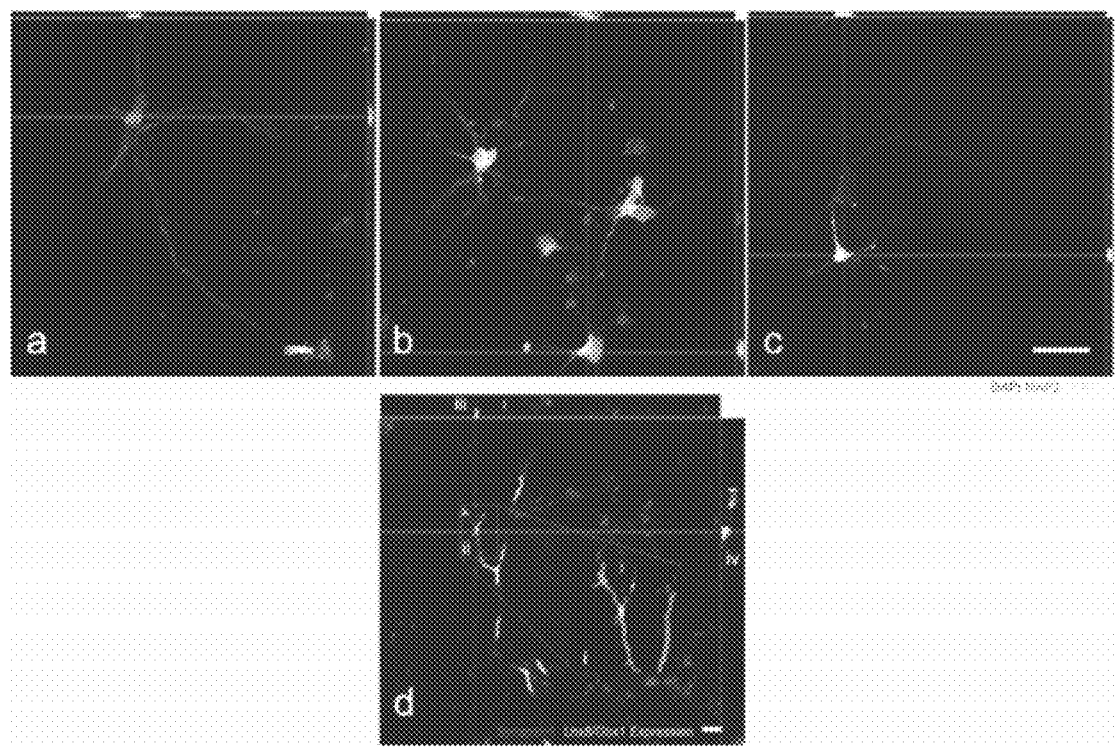
FIG. 14 shows orthogonal views of z-stacked confocal images. a,b,c: Orthogonal views of z-stacked confocal images indicate ChAT immunopositivity (green channel) is entirely encapsulated within MAP2 immunopositivity (red channel), demonstrating that ChAT immunopositivity is localized within the neurons and is neither background staining within the cells nor on their surface (side/top bar beside each image). Scale bar=20 uM. d: An orthogonal view of z-stacked confocal images confirms the generation of presynaptic terminals in nucleofected neurons expressing LhxB and Gbx1 after engrafting into murine hippocampal slice cultures. An enlarged and flattened rendering (i) of a synapse (ii), showing the total inclusion of synapsin1 within the axon. Inclusion is confirmed with individual x-axis (iii) and y-axis (iv) renderings of the synapse showing complete overlap of the punctate synapsin1 staining (red channel) within the eGFP-expressing engrafted axon. Scale bar=5 uM.
Figure 15:
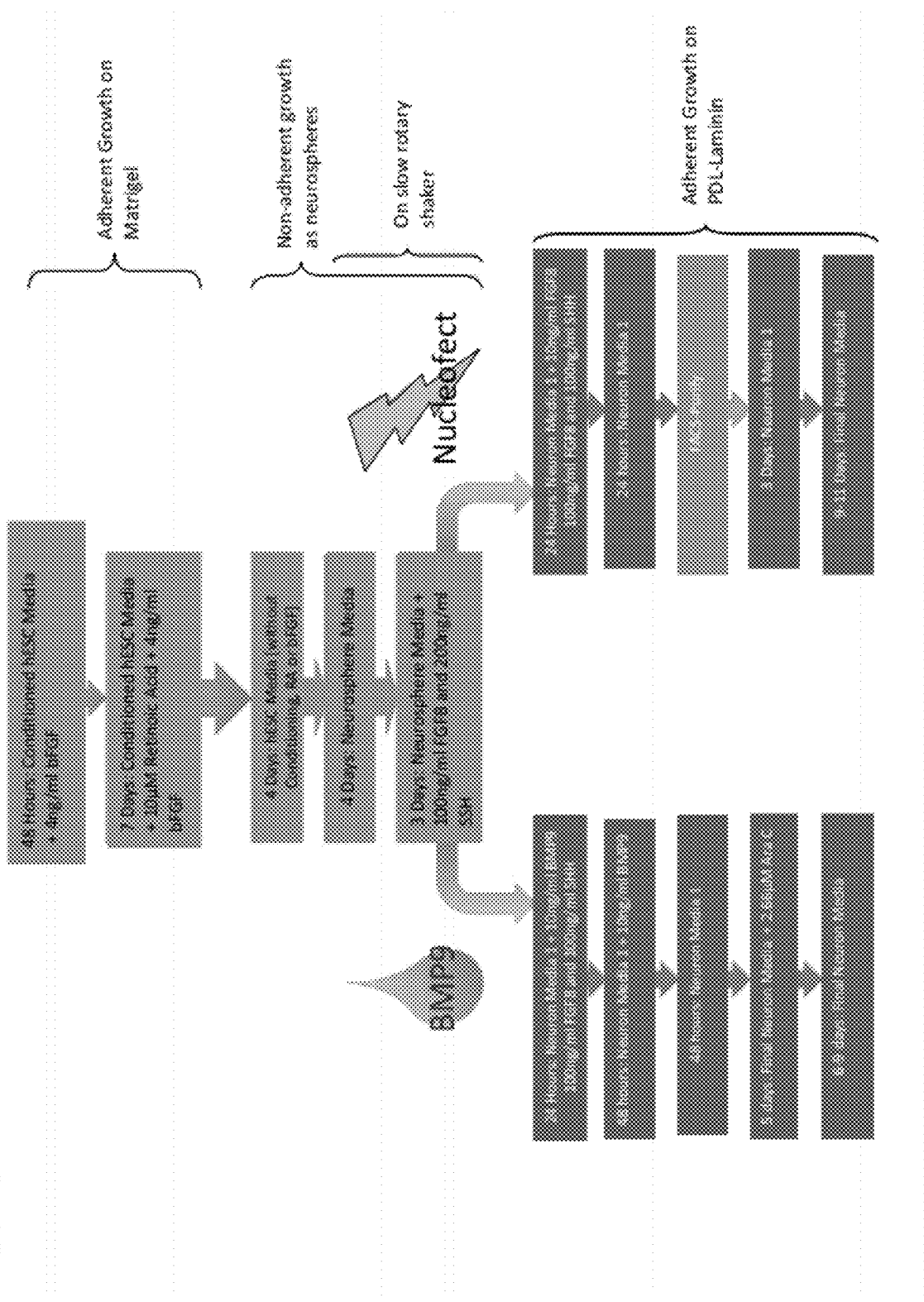
FIG. 15 shows a schematic of the timeline of media transitions.

Although neurons generated through Lhx8/Gbx1 nucleofection almost uniformly express markers characteristic of BFCN and produce acetylcholine, it remained to be determined whether these cells are functional ex vitro. To address this, a FACS-purified population was virally labeled with eGFP and allowed to engraft in entorhinal-hippocampal murine ex vivo cortical slices for 7-19 d. The cells migrated and extended long axonal projections deep into the cortical slices (FIG. 5a). These neurons continued to express markers of the BFCN lineage and formed synaptic structures with mouse cortical neurons. Immunohistochemistry for synapsin1, a marker specific for the presynaptic terminal, showed a large number of presynaptic regions directly abutting neurite outgrowths from the engrafted cells (FIG. 5b), indicating, as confirmed electrophysiologically below, that murine neurons form functional synapses with these neurons. Confocal analysis also confirmed the presence of presynaptic regions within the engrafted cells (FIG. 5c; orthogonal view confirming synapsin1 inclusion FIG. 14d), suggesting that the BFCN are initiating synaptic transmission with murine cells. To better characterize these synapses, live cultures were treated with fluorescently-conjugated α-bungarotoxin, a highly selective and permanent α7 nicotinic cholinergic receptor antagonist. Axons from the engrafted BFCN terminated on α-bungarotoxin-positive processes (FIG. 5d), confirming that these neurons are capable of generating cholinergic synapses.

Electrophysiological Function after Engraftment in Murine Slice Cultures

Figure 6:
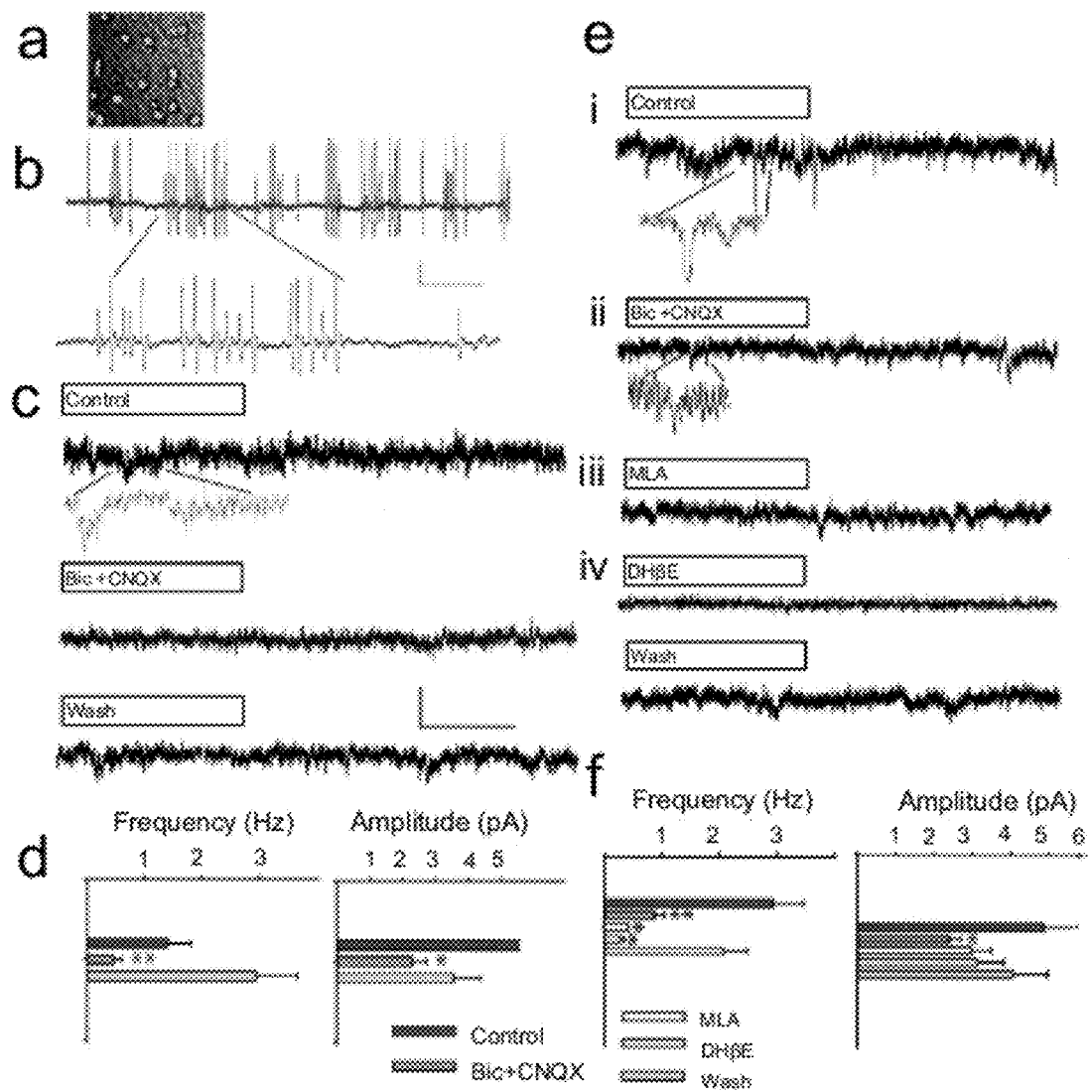
FIG. 6 show electrophysiological recordings confirm functional cholinergic neurotransmission in LhxB/Gbx1-generated basal forebrain cholinergic neurons a: Confocal microscope image of eGFP expressing neurons engrafted into mouse dentate gyrus (DG) slice cultures. b: Spontaneous action potentials in the presence of 4-AP (1OOI1M), recorded from an eGFP expressing neuron. The cell was held at −60 mVin current clamp mode, (scale bars, 200 ms, 2 pA, n=3). Lower trace illustrates action potentials from the same cell displayed on an extended scale (100 ms). c: Representative 5, traces of spontaneous GABAergic post-synaptic currents (PSCs) detected in eGFP-expressing cells under voltage clamp conditions. Using high KCl in the pipette, at −70 mV eGFP-positive cells displayed numerous PSCs. The frequency and amplitude of PSCs was significantly reduced after application of bicuculline (BIC, 100 ~M, *p<0.01, 5 out of cells) and CNQX (10 ~M). PSCs reappeared after 10 minutes washing (lower trace). d: In eGFP-expressing cells the frequency (**p<0.01) and amplitude (*p<0.05) of PSCs were significantly blocked by BIC (100~M) plus CNQX (10 J1.M, n=5) but not by methyllycaconitine (MLA, 10 nM) or dihydro-1S-erythroidine (DH~E, 1J1.M, Not Shown). e: (i) PSCs recorded from a murine neuron in close proximity to an eGFP-expressing cell. PSCs were recorded under whole cell voltage clamp (−70 m V) conditions. (ii) These PSCs were partially blocked by BIC (100 ~M) and CNQX (10~M). (iii, iv) The frequency of PSCs was further blocked by the nicotinic antagonists MLA (10 nM) and DH~E (1 ~M). (v) PSCs reappeared following washout of these drugs. f: In non-eGFP expressing cells juxtaposed to eGFP expressing cells MLA and DHβE produced a significant decrease in PSC frequency, (n=7). Error bars in d and f show s.e.m.

To demonstrate that the neurons that were generated are functional, electrophysiological recordings were performed from FACS-purified eGFP-expressing cells engrafted into hippocampal slice cultures (FIG. 6a). Recording from engrafted cells under current clamp conditions in the presence of 4-Aminopyridine (4-AP), numerous spontaneous action potentials were observed (FIG. 6b), consistent with their neuronal phenotype. Furthermore, engrafted eGFP-positive cells were observed that exhibited numerous postsynaptic currents (PSCs) under voltage clamp conditions. These currents were blocked by a combination of the GABA-A receptor antagonist bicuculline and the glutamate receptor blocker CNQX (FIG. 6c,d). No PSCs recorded from engrafted neurons were sensitive to nicotinic blocking drugs including methyllycaconitine (MLA), a blocker of α7 nicotinic receptors, or dihydro-β-erythroidine (DHβE), a blocker of α4β2 nicotinic receptors. By contrast, murine neurons in close proximity to these eGFP-expressing neurons were recorded, it was always observed that a significant percentage of PSCs were blocked by MLA or DHβE, indicating the presence of nicotinic cholinergic synapses on these cells (FIG. 6e,f), while recordings from murine neurons distal to eGFP-expressing cells never showed cholinergic PSCs (Not Shown, n=5). Thus neurons generated through Lhx8/Gbx1-overexpression are electrically excitable, being capable of generating action potentials; they receive synaptic inputs, all of which are mediated by glutamate or GABA, and they are capable of quantal release of acetylcholine at nicotinic synapses formed with other neurons: these properties establish these cells as bona fide cholinergic neurons.

Discussion

These experiments demonstrate, for example, the controlled generation of functional human BFCN from pluripotent stem cells. Treatment of hESC-derived neural progenitor cells with human orthologs of ligands known to be present in the MGE during murine embryogenesis generated a relatively pure (85%) population of these neurons. Higher yields and purity of these cells (94%) could be achieved through transient over-expression of the transcription factors Lhx8 and Gbx1 in hNSC. These neurons express all relevant markers of the BFCN lineage at both the RNA and protein levels, produce acetylcholine in vitro and do not express markers of other cholinergic lineages. Further, they generate electrophysiologically functional cholinergic synapses and spontaneous and induced action potentials ex vivo when engrafted into murine hippocampal slice cultures. Because acetylcholine produced by BFCN functions as a hippocampal neuromodulator (47, 48) it may not be necessary for transplanted neurons to replace the exact synapses lost through Alzheimer's disease related cell death in order to enhance memory function if it is only necessary to replace hippocampal cholinergic drive. These functional human cholinergic neurons thus could be use as a replacement for cells lost in Alzheimer's disease. The ability to derive these cells with high efficiency will also allow study of factors regulating the survival and function of this critical population of human neurons.

Although nucleofection experiments reliably generate a very high proportion of BFCN, the potential exists to increase the efficacy of these protocols. Altering the periods of growth in different media, especially during exposure to FGF8/SHH, has distinct consequences on the success of BMP9 treatment. Similar to the narrow spatial and temporal window of cortical BMP9 response during embryogenesis, almost no BFCN were generated either 24 hours before or after the times used here or with other departures from the protocol; further analysis of the timing or hNSC derivation might potentially increase the purity or survival of BFCN. Complete dissociation of neurospheres is important as undissociated fragments generate bFGF-responsive non-neuronal cells able to overgrow the cultures; similarly, cell cell signaling in progenitors plated at too high a density blocks their proper differentiation into BFCN. The BMP9-derived BFCN population contains some cells not committed to neuronal lineages but all cells generated from the FACS-purified nucleofections differentiated into neurons, suggesting that this population is more suitable for transplantation and might pose negligible transplantation risk; if necessary, established protocols for FACS-purification based on p75 expression (49) could remove the 6% nonBFCN neurons. These protocols were effective with the H1 hESC line in addition to the H7 hESC line used here. These studies used hESC between passage 29 and 35; BMP9 treatment had no effect on BFCN differentiation in cells above p40, and gene overexpression became progressively less efficient with increased passaging.

It remains unclear if Lhx8 and Gbx1 activity are the final mediators of signaling towards the BFCN lineage or if they are upstream of other genes along a common pathway. The differing responses of transcripts for these factors after BMP9 treatment suggests independent regulation, as does the prevalence of Gbx1 expression in presumptive BFCN in Lhx8 null mutants (38). Individual overexpression of Lhx8 or Gbx1 caused a small upregulation of the other factor but each factor individually was unable to generate cholinergic neurons. This example demonstrate that Lhx8 and Gbx1 are both necessary and sufficient to drive the differentiation of human neural progenitors into functional basal forebrain cholinergic neurons.

Methods

Generation and Programming of Neural Progenitors with BMP9 Treatment.

Figure 16:
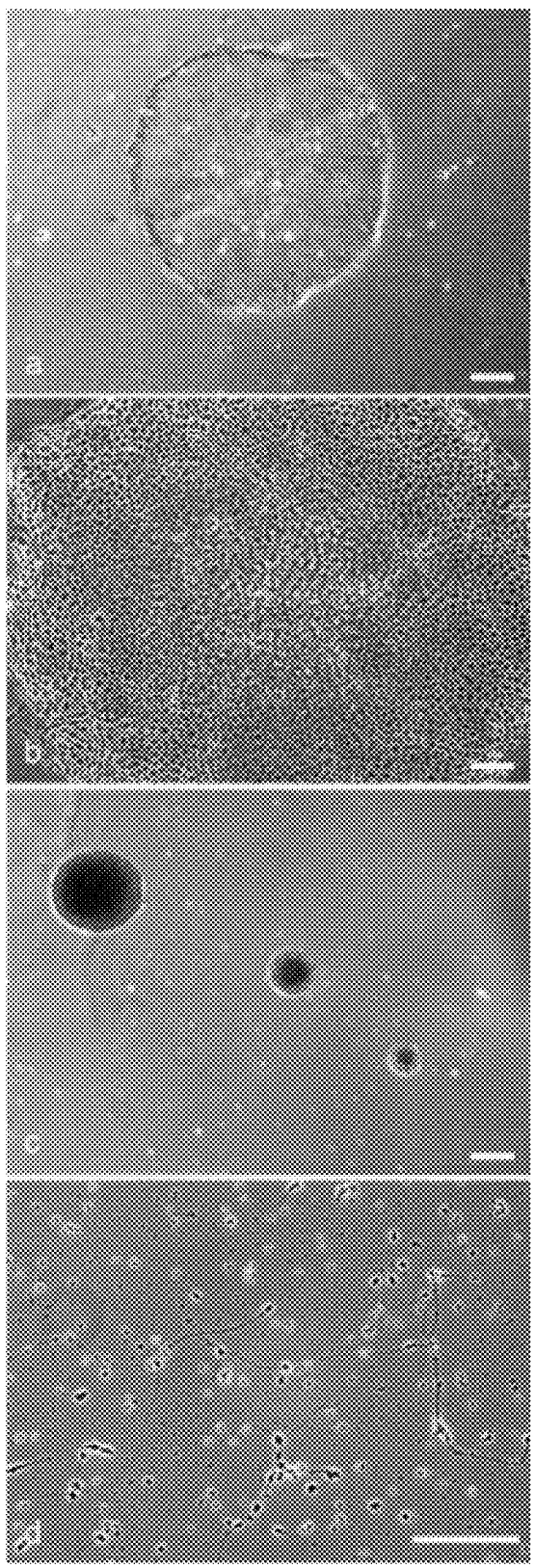
FIG. 16 shows representative images of cells during differentiation. a: Typical untreated hESC colony morphology on matrigel. Colonies with a rim of differentiating cells, internal separation between the hESC, or non-circular colony shape were discarded. b: 10 uM retinoic acid treatment alters the morphology of the hESC, generating cells with both larger nuclei and expanded cytoplasm. c: Neurospheres after 4 days in neurosphere media. d: Neurons 5 days after FACS-purification. All scale bars 200 uM.

Using retinoic acid, neural progenitors were generated from hESC using modifications of an existing protocol (43). Cells from the H7 hESC line were grown in adherent culture on matrigel in hESC media conditioned, for 24 hours on a feeder layer of 56,000 gamma-irradiated mouse embryonic fibroblasts Jcm2 and supplemented to 4 ng m$^{-1}$ bFGF. Prior to splitting, all colonies were assayed for morphology and all imperfect colonies were manually removed (FIG. 16). Two days after splitting, cells were treated with 10 μM RA in conditioned media for 7 days. Fresh RA aliquots were used every week, and RA, stock was made at 6 mM in 100% EtOH. RA-treated hESC were dissociated for 4 minutes with 5 mls accutase/10 cm dish at 370 followed by enzyme inactivation with media and gentle scraping. After pelleting at 150×G for 7 minutes, the small clumps were grown in non-adherent conditions for 4 days in hESC media without either conditioning, RA, or bFGF to begin neurosphere formation. These nascent neurosphere cultures were expanded in non-adherent dishes in neurosphere media for four days with ½ volume replaced after 48 hrs. Plates were kept on a slow rotary shaker to minimize neurosphere aggregation. Individual neurospheres were moved using a pipettor under a sterile microscope to the same media supplemented with 100 ng m$^{-1}$ FGF8 and 200 ng m$^{-1}$ SHH for 72 hrs with ½ volume replaced after 48 hrs. Neurospheres were dissociated in accutase at 37° for 10 minutes, with gentle agitation at 5 and 10 minutes, pelleted, then treated with trypsin inhibitor at 370 for a further 10 minutes. Cells were rinsed in HBSS and titrated gently through a p200 tip until all neurospheres had dissociated. Cells were plated on PDL-laminin in neuron media 1 for 5 days. For the first 24 hrs, media was supplemented with 100 ng m$^{-1}$ SHH, 100 ng m$^{-1}$ FGF8 and 10 ng ml-1 BMP9. For the next 48 hrs, media was supplemented with only B-MP9. Cells grew without additional mitogens for a subsequent 48 hrs when they were moved to neuron media 2, which has been shown optimal for the growth of murine BFCN (50), from D5 to D16-19. From D5 to D10, media was supplemented with 2.66 uM AraC to eliminate the growth of bFGF-responsive cells arising from fragments of undissociated neurospheres.

Generation of BFCN Through Nucleofection.

Figure 17:
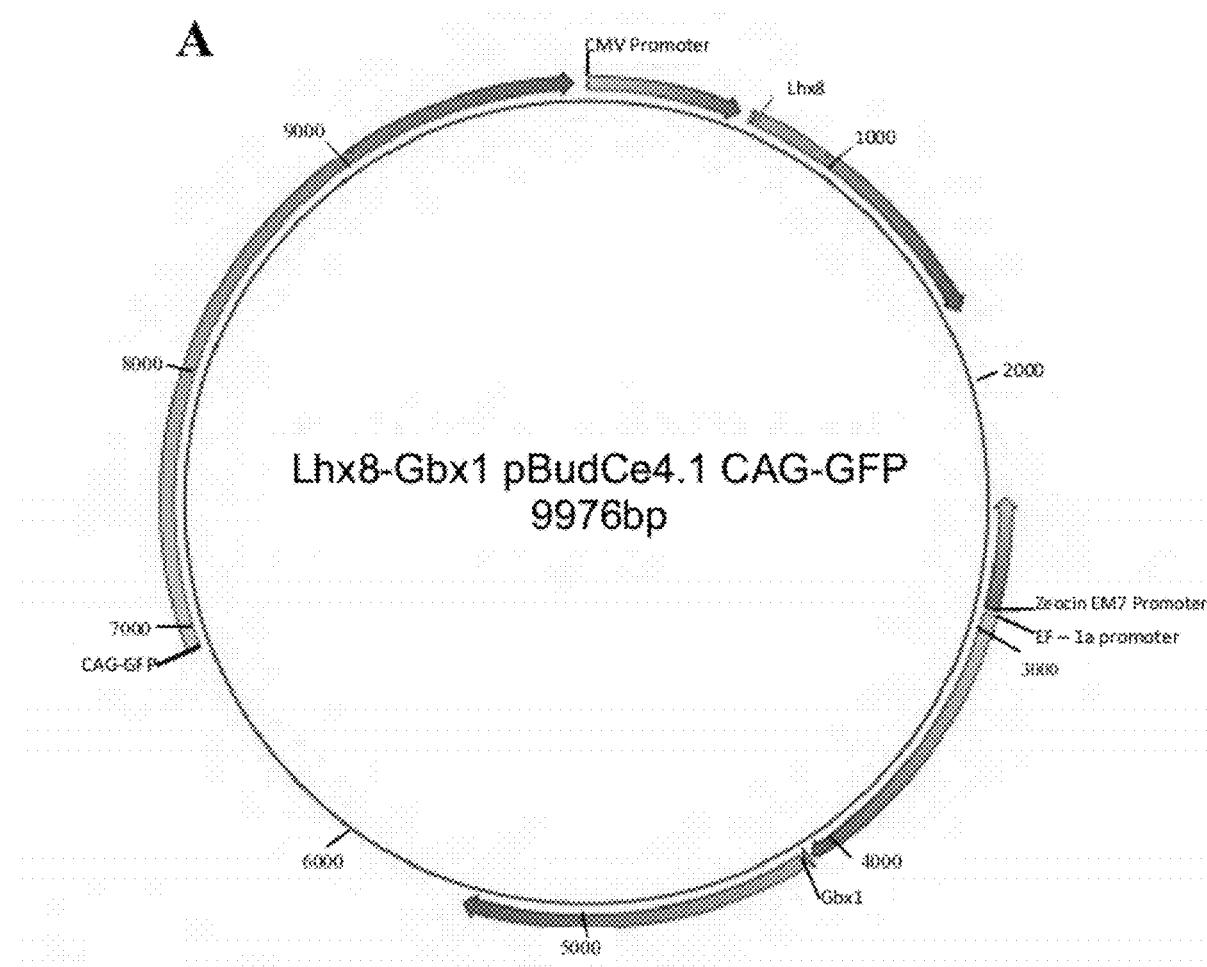
FIG. 17 shows expression vector used for transcription factor overexpression. a: A vector based on the pBudCe4.1 backbone (Invitrogen) was generated to express LhxB from the CMV promoter and Gbx1 from the EF-1a promoter. A constitutively active CAGGFP cassette was added into the vector backbone to allow FACS-purification, as either a GFP-fusion construct or IRES sequence could have altered gene function or expression levels. b: 24 hours after nucleofection, expression levels of LhxB and Gbx1 increase by 1,002.93× and 948.83× when compared with nucleofection of the GFP-only empty vector control, indicating that all three promoters cause functional transcription in the hNSC used for these experiments.
Figure 17:
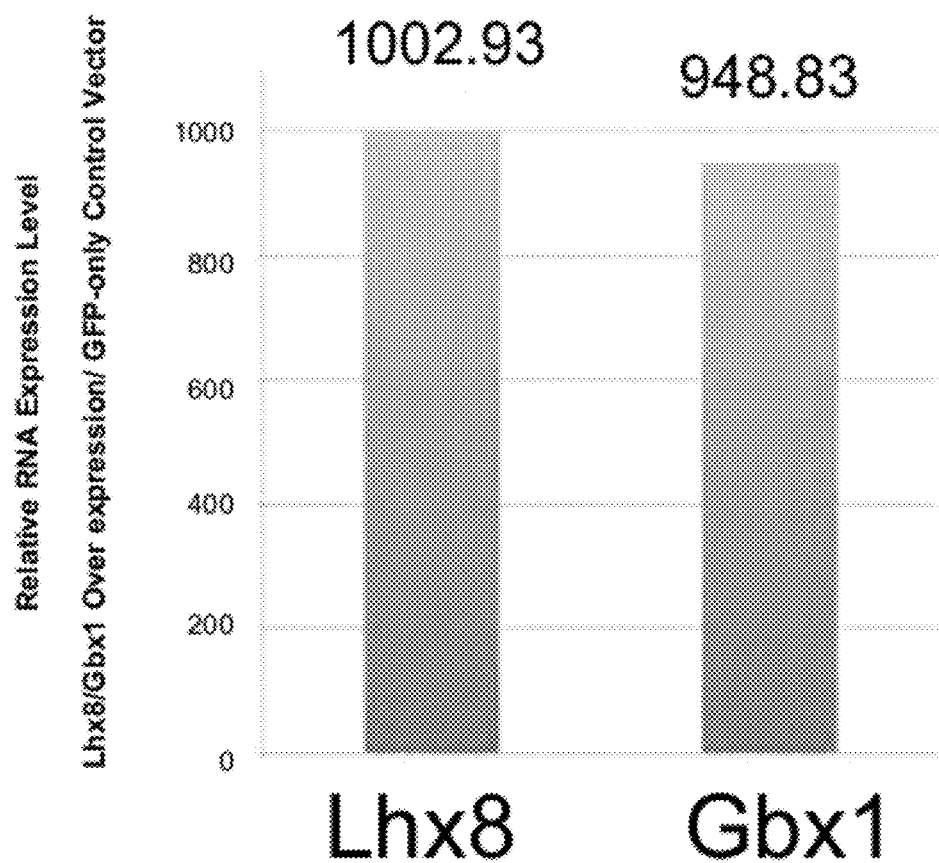

For nucleofections, 4 ug of DNA was used (a plasmid encoding both Lhx8 and Gbx1 expressed from separate promoters with a third promoter driving eGFP (FIG. 17) in hESC Nucleofection Solution-1 (Lonza) with program C-30 on an Amaxa nucleofector. Neurospheres were similarly pretreated for 72 hours in FGF8 and SHH, and were again plated into 100 ng ml⁻¹ SHH and 100 ng ml⁻¹ FGF8 for 24 hours following nucleofection, but in the absence of BMP9. Control neurons were nucleofected with the same vector without the Lhx8 and Gbx1 sequences. After 48 hours the neurons were detached with a combination of accutase and trypsin, then FACS-purified at low pressure using a Beckman Coulter MoFlo after gating to exclude debris and dead cells. Neurons were grown in the same media for the same periods as the BMP9 cells above, but without the AraC treatment as all of the FACS-purified cells differentiated following transcription factor expression.

then reverse transcribed with Thermoscript for 90 minutes (Invitrogen). qRT-PCR was performed using an Eppendorf Realplex thermocycler and SybrGreen mastermix (Applied Biosystems). Before harvesting, all neurons were grown without NGF for 48 hrs and then again with NGF for the last 24 hrs; because ChAT is a 2.1 kb (kilo base pair) cDNA comprising 15 exons spliced from a 56 kb locus it is very stable and thus has low basal expression levels: this transient NGF withdrawal allows for accurate determination of gene expression levels. The sequences for all qRT-PCR primers are provided (Table 1).

TABLE 1

|  | Forward | Reverse | SEQ ID NOs: |
|---|---|---|---|
| Acetylcholinesterase | GGAACCGCTTCCTCCCCAAATTG | TGCTGTAGTGGTCGAACTGGTTCTTC | SEQs 4 and 5 |
| β-III Tubulin | ATCAGCGTCTACTACAACGAGGCC | CAAAGATGAAATTGTCAGGCCTGAAGAGATGT | SEQs 6 and 7 |
| CNPase | AAGATGGACTTGGTCACCTACTTTGGAAAG | CGTCTTGGGTGTCACAAAGAGGG | SEQs 8 and 9 |
| ChAT 5' | TGCCGCCTACTGAGAGCAA | GTGGCAGGAGTCAAGGTTGGT | SEQs 10 and 11 |
| ChAT 3' | CATGAAGCAATACTATGGGCTCTTCTCCTC | GACGGCGGAAATTAATGACAACATCCAAG | SEQs 12 and 13 |
| GAD1 | CCAGAAAACTGGGGCTCAAGATCTG | GCAAACAGATTAGAGAAGTCAGTCTCTGTGC | SEQs 14 and 15 |
| GAPDH | GAGCACAAGAGGAAGAGAGAGACCC | GTTGAGCACAGGGTACTTTATTGATGGTACATG | SEQs 16 and 17 |
| Gbx1 | GCTGGAAGCTGATGAGCTGCT | CTTCTCCTCATCTGAGCTGTACACCTTC | SEQs 18 and 19 |
| Gbx1 Endogenous | GAAACCCCAAGATTGTTGTCCCCATAC | CAGATCCCTCGCCTTCCTAAGTTCTTG | SEQs 20 and 21 |
| GFAP | CTGGATCTGGAGAGGAAGATTGAGTCG | CTCATACTGCGTGCGGATCTCTTTCA | SEQs 22 and 23 |
| Islet1 | TGAAATGTGCGGAGTGTAATCAGTATTTGGAC | CACACAGCGGAAACACTCGATGTG | SEQs 24 and 25 |
| Lhx8 | GTTTCAGAATTGTAGAGCACGCCACAAG | CTATGCAGCGCAGTTAACATCGTTCC | SEQs 26 and 27 |
| Lhx8 Endogenous | GTTACCCCATTCAATGACACAACTGCC | CAGCAAAGTGATGTTGGAAATGCTTTAGGTG | SEQs 28 and 29 |
| Lhx6 | CACGGCTACATCGAGAGTCAGGTAC | CAATCTGGCTCCATTTACCTTCTCAC | SEQs 30 and 31 |
| Nkx2.1 | CTACTGCAACGGCAACCTGGG | CCATGAAGCGGGAGATGGCG | SEQs 32 and 33 |
| NOS | CAGGCTGTGACTGATGACCACATC | AGGTCATGTTTGGAGATGACCCTTGAG | SEQs 34 and 35 |
| P75NTR | GGAGAAAAACTCCACAGCGACAGTG | AGAGCCGTTGAGAAGCTTCTCCAC | SEQs 36 and 37 |
| Somatostatin | CAGACTCCGTCAGITTCTGCAGAAG | CTTCAGGTTCCAGGGCATCATTCTC | SEQs 38 and 39 |
| TrkA | GAGGTCTCTGTTCAGGTCAACGTCT | CTCAGTGAAGATGAAGCTGGTCTCATTGA | SEQs 40 and 41 |
| Tyrosine Hydroxylase | AGTGTCATCACCTGGTCACCAAGTTC | CTTCAGCGTGGTGTAGACCTCCTT | SEQs 42 and 43 |
| VGlut1 | GCTACATTGTCACTCAGATTCCAGGAGG | ATCCTCACGAAGATGACACAGCCATAG | SEQs 44 and 45 | qRT-PCR primer sequences. All primers have a melting temperature of 60° ± 0.3°. All primer sets (except GAPDH) span an intron.

siRNA Studies.

100 pg (5 ul of 20 nM stock) of Dharmacon ON-TARGETplus SMARTpool siRNA specific to human Lhx8 was used for each replicate siRNA nucleofection, while control replicates received an equal amount of scrambled non-specific ON-TARGETplus Non-Targeting Pool. To determine siRNA nucleofection efficiency, an equivalent amount of siGLO Red Transfection Indicator siRNA was used in separate experiments. To show the efficacy of the Lhx8 siRNA, dissociated neurospheres were nucleofected with either Lhx8 specific or non-targeting siRNA, plated for 6 hours, then treated with BMP9 for 6 hours before harvesting the cells for RNA.

Cell Analysis.

RNA was extracted with the RNAqueous-4PCR kit (Ambion), treated with TurboDNAse (Ambion) for 30 minutes, Cells for immunohistochemistry were rinsed in 4% (wt/vol) PFA (paraformaldehyde) then fixed in 4% PFA for 20 minutes followed by 30 minutes of permeabilization with 0.10% (vol/vol) Triton X-100 (Sigma). After blocking in 10% (vol/vol) goat serum for 30 minutes, primary antibodies (ChAT 1:666 Ayes Labs, Map2 1:500 Abcam, p75 1:666 Abcam, VChAT 1:250 SYSY, VGlut 1:3000 SYSY, HB9 1:1000 Abcam, GFAP 1:1000 Sigma, GFP 1:500 Abcam, MBP 1:666 Sternberger Monoclonals Inc., Synapsin 1:500 SYSY, FORSE1 1:75 Developmental Studies Hybridoma Bank, Nestin 1:500 Abcam) were added for 60 minutes at room temperature. Appropriate fluorescent secondary antibodies (Ayes Labs (FITC)-conjugated anti-Chicken IgY 1:500 for ChAT, Molecular Probes 1:1000 for all others) were added for 45 minutes. All photomicroscopy and counts of ChAT, p75, Map2, synapsin1, α-bungarotoxin, and HB9 were performed using a Zeiss LSM 510UV META laser scanning confocal microscope while VChat, VGlut, GFAP and MBP analysis used a Zeiss epifluorescence microscope. Acetylcholine levels in cultured neurons were determined with an AmplexRed detection kit (Invitrogen) and correlated with protein levels determined using the FluoroProfile Protein Quantification Kit (Sigma). For α-bungarotoxin labeling, live murine cortical cultures with engrafted BFCN were rinsed with HBSS, incubated with 3 mls 0.05 mg ml-1-1 AlexaFluor594-conjugated a-bungarotoxin (Invitrogen) for 30 minutes in final neuron media, rinsed in HBSS, rinsed in 0.1% Triton X-100 in PBS, then fixed in 4% PFA for 30 minutes.

Preparation of Murine Organotypic Hippocampal Slice Culture.

P5-P6 CD1 mice were chilled on ice and sacrificed by decapitation; brains were removed under aseptic conditions followed by the separation of the hippocampus and enthorinal cortex (HEC) from the two hemispheres as previously described (50). The HEC tissue blocks were cut using a McIlwain tissue chopper into 350 11 m-thick coronal slices. Slices were placed on semiporous membrane inserts (Millicell-CM, 0.4 11 m) and transferred to six-well culture plates with 1.2 ml of MEM supplemented with 25% (vol/vol) horse serum, 6.5 mg ml$^{-1}$ D glucose, and 0.5 mM L-glutamine. After 3-4 d in culture, the medium was changed to final neuron media supplemented with 40/0 knockout serum replacement, and the media changed every 72 hrs.

Micrografting of BFCN Derived from HESC into Murine Slice Cultures.

Presumptive BFCN generated through Lhx8/Gbx1 nucleofection were FACS-purified at 48 hours and subsequently grown in culture for 5-7 days. To maintain fluorescent signal intensity beyond that from the transient nucleofection, purified cells were permanently labeled with an adenovirus encoding eGFP. Cultures were dissociated using accutase, counted, and loaded on the tip of a 0.5 µl Hamilton syringe mounted on a micromanipulator. After the slices had been transferred into the serum-supplemented final neuron media, suspensions of these FACS-purified cells (3-4,000 cells/0.2 ul) were seeded locally onto the murine hippocampal cultures in the area of the dentate gyrus (DG). After 2-3 d in culture, grafted cells were continuously monitored for GFP fluorescence using live confocal microscopy and processed for electrophysiological recording and eventual immunohistochemistry.

Electrophysiological Recordings of BFCN Derived from hESC into Murine Slice Cultures.

Organotypic slice cultures 2-19 days old were incubated for 30 min at 37° C. in oxygenated standard artificial CSF (ACSFl containing (in mM): 130 NaCl, 24 NaHC03, 3.5 KCt 1.25 NaH2P04, 1.5 CaCl2, 1 MgS04, and 10 glucose, saturated with 95% 02 and 5% C02 at pH 7.4 and then maintained at room temperature until being transferred to the recording chamber in oxygenated standard ACSF. The eGFP-positive engrafted cells were observed with the aid of a fluorescence microscope (BX-50WI; Olympus) and visualized with a chilled charge-coupled device video camera (Dage-MTI) with a 40× water-immersion differential interference contrast objective. Whole cell patch clamp recordings were performed either from eGFP-expressing cells or neighboring murine cells (not eGFPexpressing) located in the subgranular zone of the dentate gyrus. For whole cell voltage clamp recordings, patch electrodes with a resistance of 5-7 MΩ were pulled from borosilicate capillaries (World Precision Instruments; PG52165-glass). Patch pipettes were filled with a solution of (in mM) 150 KCt 10 HEPES, 4 Mg2ATP, 0.5 NaGTP, and 10 phosphocreatine. The pH was adjusted to 7.3 with KOH. For whole cell current clamp experiments the pipette solution was potassium gluconate, 100; EGTA, 10; MgCl2, 5; Hepes, 40; ATP, 3; GTP, 0.3; pH adjusted to 7.2 with KOH and osmolarity to 295 mOsm with sucrose. Whole-cell voltage clamped recordings were obtained from the fluorescence-labeled cells using an Axopatch 200B patch-clamp amplifier (Molecular Devices) and the data were captured with pClamp 9.0 software (Molecular Devices).

Data Analysis.

Data were filtered at 2 kHz and digitized at 10 kHz using a Digidata 1322A analog-to-digital board. Analysis was performed using the pClamp 9.0 (Molecular Devices), MiniAnalysis (Synaptosoft), or Sigmaplot. For the detection and measurement of PSCs, all PSCs were detected in 1-3 min recording segments under the appropriate experimental configuration (baseline control, drug application). Event frequency and amplitude were determined by MiniAnalysis software (Synaptosoft).

Drugs Used

Bicuculline methiodide, 6-cyano-7-nitroquinoxaline-2,3-dione (CNQX), dihydro-β-erythroidine HBr (DHbE), methyllycaconnitine (MLA), 4-aminopyridine (4-AP) (all Sigma) were applied by either focal or bath application. All experiments performed here were performed in accordance with animal experimentation protocols approved by the National Institutes of Health and institutional protocols.

Statistical Analysis.

The RNA data (FIGS. 1-3) were analyzed for statistical significance using the Analyses of Variance method CANOVA) with version 9.1 of SAS. For the counts of ChAT-positive neurons (FIG. 4), the ratios violated the assumptions of parametric hypothesis tests with respect to normal distributions and homogeneity of variance, consequently non-parametric alternative tests were carried out. The Kruskal-Wallis test was used to test the global null hypothesis that there was no significant difference between the median ratios with respect to the four groups. Mann-Whitney U tests were used to test the null hypotheses that there were no significant differences between the median ratios when pairs of treatments were compared. The decision rule was to reject the null hypothesis if the p value of each of the Kruskal-Wallis or the Mann-Whitney U tests was less than the prescribed level of significance of a=0.05. The hypothesis tests were performed using SPSS version 17.0. Paired and N on-paired Student's T-Tests were used to determine the significance of the changes in electrophyiological response following specific receptor antagonist treatment (FIG. 6d,f).

Supplemental Methods

Media Formulations (All Percents are (Vol/Vol))

hESC Media

50% DMEM-F12 (+L-Glutamine)

1% Non-essential amino acids 16.66% Knockout Serum Replacement (Invitrogen)

100 uM β-mercaptoethanol

Neurosphere Media

50% DMEM-F12 (+L-Glutamine)

1% amino acids

1% N2 supplement

100~M β-mercaptoethanol 8 ug ml$^{-1}$ Heparin 20 ng ml$^{-1}$ bFGF 20 ng ml$^{-1}$ EGF Neuron Media 1

30% DMEM-F12 (+L-glutamine)

2% B-27 Supplement 100 ng ml$^{-1}$ NGF

Neuron Media 2
Neurobasal Media
1% B-27 Supplement
0.5% Glutamax
0.5% Glutamine
20 ng ml$^{-1}$ bFGF
100 ng ml$^{-1}$ NGF

REFERENCES

1. Muir, J, L., Acetylcholine, aging, and Alzheimer's disease. Pharmacol Biochem Behav, 1997. 56(4): p. 687-96.
2. Power, A. E., A. Vazdarjanova, and I. L. McGaugh, Muscarinic cholinergic influences in memory consolidation. Neurobiol Learn Mem, 2003. 80(3).' p. 178-93.
3. Mesulam, M., et al., Cholinergic nucleus basalis tauopathy emerges early in the aging-MCl-AD continuum. Ann Neurol, 2004. 55(6): p. 815-28.
4. Mufson, E. j., et al., Loss of basal forebrain P75(NTR) immunoreactivity in subjects with mild cognitive impairment and Alzheimer's disease. I Comp Neurol, 2002. 443 (2): p. 136-53.
5. Abe, K, et al., Amnesia after a discrete basal forebrain lesion. I Neurol Neurosurg Psychiatry, 1998. 65(1): p. 126-30.
6. Salmond, C H., et al., Cognitive sequelae of head injury: involvement of basal forebrain and associated structures. Brain, 2005. 128(Pt 1): p. 189-200.
7. Benke, T., et al., Cholinergic treatment of amnesia following basal forebrain lesion due to aneurysm rupture—an open-label pilot study. Eur J Neurol, 2005. 12(10): p. 791-6.
8. Fujii, T., et al., The role of the basal forebrain in episodic memory retrieval: a positron emission tomography study. Neuroimage, 2002. 15(3): p. 501-8.
9. Easton, A., et al., Unilateral lesions of the cholinergic basal forebrain and fornix in one hemisphere and inferior temporal cortex in the opposite hemisphere produce severe learning impairments in rhesus monkeys. Cereb Cortex, 2002. 12(7): p. 729-36.
10. Book, A. A., R. G. Wiley, and). B. Schweitzer, Specificity of 192/g G-saporin for NGF receptor-positive cholinergic basal forebrain neurons in the rat. Brain Res, 1992. 590(1-2): p. 350-5.
11. Pizzo, D. P., L. I. Thai, and). Winkler, Mnemonic deficits in animals depend upon the degree of cholinergic deficit and task complexity. Exp Neurol, 2002. 177(1): p. 292-305.
12. Moreau, P. H., et al., Neuroanatomical and behavioral effects of a novel version of the cholinergic immunotoxin mu p75-saporin in mice. Hippocampus, 2008. 18(6): p. 610-22.
13. Mohapel, P., et al., Forebrain acetylcholine regulates adult hippocampal neurogenesis and learning. Neurobiol Aging, 2005. 26(6): p. 939-46.
14. Kaneko, N., H. Okano, and K Sawamoto, Role of the cholinergic system in regulating survival of newborn neurons in the adult mouse dentate gyrus and olfactory bulb. Genes Cells, 2006. 11(10): p. 1145-59.
15. Cooper-Kuhn, C M.,). Winkler, and H. G. Kuhn, Decreased neurogenesis after cholinergic forebrain lesion in the adult rat.) Neurosci Res, 2004. 77(2): p. 155-65.
16. Conner,). M., et al., Lesions of the Basal forebrain cholinergic system impair task acquisition and abolish cortical plasticity associated with motor skill learning. Neuron, 2003. 38(5): p. 819-29.
17. Conner,). M., A. A. Chiba, and M. H. Tuszynski, The basal forebrain cholinergic system is essential for cortical plasticity and functional recovery following brain injury. Neuron, 2005. 46(2): p. 173-9.
18. Kuczewski, N., et al., Selective cholinergic immunolesioning affects synaptic plasticity in developing visual cortex. Eur J Neurosci, 2005. 21(7): p. 1807-14.
19. Ma, X and N. Suga, Augmentation of plasticity of the central auditory system by the basalforebrain and/or somatosensory cortex.) NeurophysioL 2003. 89(1): p. 90-103.
20. Thiel, C M., K). Friston, and R. I. Dolan, Cholinergic modulation of experience dependent plasticity in human auditory cortex. Neuron, 2002. 35(3): p. 567-74.
21. Sweeney,). E., et al., Neurogenesis of the basal forebrain in euploid and trisomy 16 mice: an animal model for developmental disorders in Down syndrome. Neuroscience, 1989. 31(2): p. 413-25.
22. Schambra, U. B., et al., Ontogeny of cholinergic neurons in the mouse forebrain.) Comp Neural, 1989. 288(1): p. 101-22.
23. Li, Y., et al., Regulation of TrkA and ChAT expression in developing rat basal forebrain: evidence that both exogenous and endogenous NGF regulate differentiation of cholinergic neurons. J Neurosci, 1995. 15(4): p. 2888-905.
24. Sofroniew, M. v., et al., Survival of adult basal forebrain cholinergic neurons after loss of target neurons. Science, 1990. 247(4940): p. 338-42.
25. Mufson, E.)., et al., Human cholinergic basal forebrain: chemoanatomy and neurologic dysfunction. J Chem Neuroanat, 2003. 26(4): p. 233-42.
26. Smeyne, R. j., et al., Severe sensory and sympathetic neuropathies in mice carrying a disrupted Trk/NGF receptor gene. Nature, 1994. 368(6468): p. 246-9.
27. Lee, K F., et al., Targeted mutation of the gene encoding the low affinity NGF receptor p75 leads to deficits in the peripheral sensory nervous system. Cell, 1992. 69(5): p. 737-49.
28. Van der Zee, C E. and T. Hagg, p75NGFR mediates death of cholinergic neurons during postnatal development of the neostriatum in mice. J Chem Neuroanat, 1998. 14{3-4): p. 129-40.
29. Crowley, C, et al., Mice lacking nerve growth factor display perinatal loss of sensory and sympathetic neurons yet develop basal forebrain cholinergic neurons. Cell, 1994. 76(6): p. 1001-11.
30. Song, J. J., et al., Bone morphogenetic protein-9 binds to liver cells and stimulates proliferation. Endocrinology, 1995. 136{1 0): p. 4293-7.
31. Lopez-Coviella, I., et al., Induction and maintenance of the neuronal cholinergic phenotype in the central nervous system by BMP-9. Science, 2000. 289(5477): p. 313-6.
32. Lopez-Coviella, I., et al., Bone morphogenetic protein 9 induces the transcriptome of basalforebrain cholinergic neurons. Proc Natl Acad Sci USA, 2005. 102(19): p. 6984-9.
33. Matsumoto, K, et al., L3, a novel murine LIM-homeodomain transcription factor expressed in the ventral telencephalon and the mesenchyme surrounding the oral cavity. Neurosci Lett, 1996. 204{1-2): p. 113-6.
34. Grigoriou, M., et al., Expression and regulation of Lhx6 and Lhx7, a novel subfamily of LIM homeodomain encoding genes, suggests a role in mammalian head development. Development, 1998. 125(11): p. 2063-74.
35. Asbreuk, C H., et al., The homeobox genes Lhx7 and Gbx1 are expressed in the basalforebrain cholinergic system. Neuroscience, 2002. 109(2): p. 287-98.

36. Nobrega-Pereira, S., et al., Postmitotic Nkx2-1 controls the migration of telencephalic interneurons by direct repression of guidance receptors. Neuron, 2008. 59(5): p. 733-45.
37. Zhao, Y., et al., Isolated cleft palate in mice with a targeted mutation of the LIM homeoboxygene Lhx8. Proc Natl Acad Sci USA, 1999. 96(26): p. 15002-6.
38. Zhao, Y., et al., The LIM-homeobox gene Lhx8 is required for the development of many cholinergic neurons in the mouse forebrain. Proc Natl Acad Sci USA, 2003. 100(15): p. 9005-10.
39. Mori, T., et al., The LIM homeobox gene, L3/Lhx8, is necessary for proper development of basal forebrain cholinergic neurons. Eur J Neurosci, 2004. 19(12): p. 3129-41.
40. Fragkouli, A., et al., Loss of forebrain cholinergic neurons and impairment in spatial learning and memory in LHX7-deficient mice. Eur j Neurosci, 2005. 21(11): p. 2923-38.
41. Price, M., et al., Regional expression of the homeobox gene Nkx-2.2 in the developing mammalian forebrain. Neuron, 1992. 8(2): p. 241-55.
42. Sussel, L., et al., Loss of Nkx2.1 homeobox gene function results in a ventral to dorsal molecular respecification within the basal telencephalon: evidence for a transformation of the pallidum into the striatum. Development, 1999. 126(15): p. 3359-70.
43. Doering, L. e. and E. Y. Snyder, Cholinergic expression by a neural stem cell line grafted to the adult medial septum/diagonal band complex. j Neurosci Res, 2000. 61(6): p. 597-604.
44. Rhinn, M., A. Picker, and M. Brand, Global and local mechanisms of forebrain and midbrain patterning. Curr Opin Neurobiol, 2006. 16(1): p. 5-12.
45. Tucker, E. S., et al., Molecular specification and patterning of progenitor cells in the lateral and medial ganglionic eminences. j Neurosci, 2008. 28(38): p. 9504-18.
46. Allendoerfer, K. L., j. L. Magnani, and P. H. Patterson, FORSE-1, an antibody that labels regionally restricted subpopulations of progenitor cells in the embryonic central nervous system, recognizes the Le(x) carbohydrate on a proteoglycan and two glycolipid antigens. Mol Cell Neurosci, 1995. 6(4): p. 381-95.
47. Disterhoft, j. F. and M. M. Oh, Pharmacological and molecular enhancement of learning in aging and Alzheimer's disease. j Physiol Paris, 2006. 99(2-3): p. 180-92.
48. Lawrence, j. f., Cholinergic control of GABA release: emerging parallels between neocortex and hippocampus. Trends Neurosci, 2008. 31(7): p. 317-27.
49. Schnitzler, A. e., /. Lopez-Coviella, and j. K Blusztajn, Purification and culture of nerve growth factor receptor (p75)-expressing basal forebrain cholinergic neurons. Nat Protoc, 2008. 3(1): p. 34-40.
50. Belmadani, A., et al., Ethanol pre-exposure suppresses HIV-1 glycoprotein 120-induced neuronal degeneration by abrogating endogenous glutamate/Ca2+ mediated neurotoxicity. Neuroscience, 2001. 104(3): p. 769-81.

All publications and patents mentioned in the present application are herein incorporated by reference. Various modification and variation of the described methods and compositions of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the relevant fields are intended to be within the scope of the following claims.

We claim:

1. A method of generating basal forebrain cholinergic neurons (BFCNs) in vitro comprising: treating isolated neural progenitor cells with: i) an effective amount of FGF8, or a biologically active fragment or variant thereof, and ii) an effective amount of Sonic Hedgehog (SHH) or a biologically active fragment or variant thereof, wherein said treating generates BFCNs.

2. The method of claim 1, further comprising generating said neural progenitor cells by treating embryonic stem cells with retinoic acid.

3. The method of claim 1, wherein said FGF8 and SHH are human.

4. The method of claim 1, wherein said neural progenitor cells are human neural progenitor cells.

5. The method of claim 1, further comprising treating said neural progenitor cells with BMP9.

6. The method of claim 1, further comprising transfecting said neural progenitor cells with vectors encoding Gbx1 and/or Lhx8.

* * * * *

SEQUENCE LISTING

<160> NUMBER OF SEQ ID NOS: 45

<210> SEQ ID NO 1
<211> LENGTH: 1320
<212> TYPE: DNA
<213> ORGANISM: Homo sapiens

<400> SEQUENCE: 1

```
atgagtccgg agggcgacac ccccagcccg cctgctcgcc cgcccctcc ttatgagaga      60 gagggagcgc ggcgccggag ccacactgcg ccgagcccgc gccccgccgc cacctcggcc     120
cgggagccag ggagcgagcc ctgcgtgtcc gcgcggggcg cccgagccgc ggggcgcacg     180
gaggcgccca gagaggagcg ccccggggcg gccgcagctc cgaacaagat gcagcgggcc     240
ggaggcggta gcgcccctgg gggcaacggc ggggcggcg gcggggccc gggcactgcc      300 ttctccatcg actccctaat cgggccgccg ccgccgcgct ccggccactt gctgtacacc     360
ggctacccca tgttcatgcc ctaccggccg ctcgtgctgc cgcaggcgct ggcccctgcg     420
ccgctgcccg ctggcctccc gccctcgcc ccgctagcct ctttcgccgg ccgccttacc      480
aacaccttct gcgcggggct gggtcaggct gtgccctcga tggtggcgct gaccaccgcg     540
ctgcccagct tcgcggagcc gcccgacgct ttctacgggc cccaggagct cgccgccgcc     600
gctgccgccg ccgccgccac tgccgcccga aacaaccccg agccaggcgg ccgacgccca     660
gagggtgggc tggaagctga tgagctgctg ccggccgggg agaaagtggc agagccccca     720
ccacctccgc ctccgcactt ctcagagact tttccaagtc tgcccgcaga ggggaaggtg     780
```

-continued

```
tacagctcag atgaggagaa gctggaggca tcagcaggag acccagcagg cagcgaacag    840
gaggaagagg gctcaggcgg tgacagcgag gatgacggtt tcctggacag ttctgcaggg    900
ggcccagggg ctcttctggg acctaaaccg aagctaaagg gaagcctggg gactggagct    960
gaggaggggg caccggtgac agcagggtc acagctcctg gggggaaaag ccgacggcgc    1020
cgcacagcat ttaccagcga gcagcttttg gaattggaga aggaatttca ttgcaagaaa    1080
tacctgagct tgacagagcg ctctcagatc gcccacgccc tcaagctcag tgaggtgcag    1140
gtcaagatct ggtttcagaa tcgacgggcc aagtggaagc gcatcaaagc tggcaatgtg    1200
agcagccgtt ctggggagcc cgtaagaaac cccaagattg ttgtccccat acctgtgcat    1260
gtcaacaggt ttgctgtgcg gagccagcac caacaaatgg agcaggggc ccggccctga    1320
```

<210> SEQ ID NO 2
<211> LENGTH: 439
<212> TYPE: PRT
<213> ORGANISM: Homo sapiens

<400> SEQUENCE: 2

```
Met Ser Pro Glu Gly Asp Thr Pro Ser Pro Pro Ala Arg Pro Pro Pro
1               5                   10                  15

Pro Tyr Glu Arg Glu Gly Ala Arg Arg Ser His Thr Ala Pro Ser
            20                  25                  30

Pro Arg Pro Ala Ala Thr Ser Ala Arg Glu Pro Gly Ser Glu Pro Cys
        35                  40                  45

Val Ser Ala Arg Gly Ala Arg Ala Ala Gly Arg Thr Glu Ala Pro Arg
    50                  55                  60

Glu Glu Arg Pro Gly Ala Ala Ala Ala Pro Asn Lys Met Gln Arg Ala
65                  70                  75                  80

Gly Gly Gly Ser Ala Pro Gly Gly Asn Gly Gly Gly Gly Gly Gly
                85                  90                  95

Pro Gly Thr Ala Phe Ser Ile Asp Ser Leu Ile Gly Pro Pro Pro
            100                 105                 110

Arg Ser Gly His Leu Leu Tyr Thr Gly Tyr Pro Met Phe Met Pro Tyr
        115                 120                 125

Arg Pro Leu Val Leu Pro Gln Ala Leu Ala Pro Ala Pro Leu Pro Ala
    130                 135                 140

Gly Leu Pro Pro Leu Ala Pro Leu Ala Ser Phe Ala Gly Arg Leu Thr
145                 150                 155                 160

Asn Thr Phe Cys Ala Gly Leu Gly Gln Ala Val Pro Ser Met Val Ala
                165                 170                 175

Leu Thr Thr Ala Leu Pro Ser Phe Ala Glu Pro Pro Asp Ala Phe Tyr
            180                 185                 190

Gly Pro Gln Glu Leu Ala Ala Ala Ala Ala Ala Ala Ala Thr Ala
        195                 200                 205

Ala Arg Asn Asn Pro Glu Pro Gly Gly Arg Arg Pro Glu Gly Gly Leu
    210                 215                 220

Glu Ala Asp Glu Leu Leu Pro Ala Arg Glu Lys Val Ala Glu Pro Pro
225                 230                 235                 240

Pro Pro Pro Pro His Phe Ser Glu Thr Phe Pro Ser Leu Pro Ala
                245                 250                 255

Glu Gly Lys Val Tyr Ser Ser Asp Glu Glu Lys Leu Glu Ala Ser Ala
            260                 265                 270

Gly Asp Pro Ala Gly Ser Glu Gln Glu Glu Glu Gly Ser Gly Gly Asp
        275                 280                 285
```

```
Ser Glu Asp Asp Gly Phe Leu Asp Ser Ser Ala Gly Gly Pro Gly Ala
    290                 295                 300

Leu Leu Gly Pro Lys Pro Lys Leu Lys Gly Ser Leu Gly Thr Gly Ala
305                 310                 315                 320

Glu Glu Gly Ala Pro Val Thr Ala Gly Val Thr Ala Pro Gly Gly Lys
                325                 330                 335

Ser Arg Arg Arg Thr Ala Phe Thr Ser Glu Gln Leu Leu Glu Leu
                340                 345                 350

Glu Lys Glu Phe His Cys Lys Lys Tyr Leu Ser Leu Thr Glu Arg Ser
            355                 360                 365

Gln Ile Ala His Ala Leu Lys Leu Ser Glu Val Gln Val Lys Ile Trp
370                 375                 380

Phe Gln Asn Arg Arg Ala Lys Trp Lys Arg Ile Lys Ala Gly Asn Val
385                 390                 395                 400

Ser Ser Arg Ser Gly Glu Pro Val Arg Asn Pro Lys Ile Val Val Pro
                405                 410                 415

Ile Pro Val His Val Asn Arg Phe Ala Val Arg Ser Gln His Gln Gln
            420                 425                 430

Met Glu Gln Gly Ala Arg Pro
                435

<210> SEQ ID NO 3
<211> LENGTH: 418
<212> TYPE: PRT
<213> ORGANISM: Mus musculus

<400> SEQUENCE: 3

Met Ser Pro Glu Gly Asp Thr Pro Asn Pro Ala Arg Pro Leu Pro
1               5                   10                  15

Pro Tyr Glu Arg Glu Ser Ala Ala Pro Glu Pro His Cys Ala Glu Pro
                20                  25                  30

Ala Pro Arg Arg His Leu Gly Pro Arg Ala Arg Ser Glu Pro Cys Val
            35                  40                  45

Ser Ala Arg Gly Ala Arg Arg Gly Pro Gly Ser Ala Met Gln Arg Ala
    50                  55                  60

Ala Gly Gly Gly Ala Pro Gly Gly Ser Gly Ser Ser Gly Gly Pro
65                  70                  75                  80

Gly Ala Ala Phe Ser Ile Asp Ser Leu Ile Gly Pro Pro Pro Pro Arg
                85                  90                  95

Ser Gly His Leu Leu Tyr Thr Gly Tyr Pro Met Phe Met Pro Tyr Arg
                100                 105                 110

Pro Leu Val Leu Pro Gln Ala Leu Ala Pro Ala Pro Leu Pro Ala Gly
            115                 120                 125

Leu Pro Pro Leu Ala Pro Leu Ala Ser Phe Ala Gly Arg Leu Ser Asn
130                 135                 140

Thr Phe Cys Ala Gly Leu Gly Gln Ala Val Pro Ser Met Val Ala Leu
145                 150                 155                 160

Thr Thr Ala Leu Pro Ser Phe Ala Glu Pro Pro Asp Ala Tyr Tyr Gly
                165                 170                 175

Pro Pro Glu Leu Ala Ala Ala Ala Ser Thr Ala Ser Arg Ser Asn
                180                 185                 190

Pro Glu Pro Ala Ala Arg Arg Thr Asp Gly Ala Leu Asp Ala Glu Glu
            195                 200                 205

Leu Leu Pro Ala Arg Glu Lys Val Thr Glu Pro Pro Pro Pro Pro Pro
```

```
                        210                 215                 220
Pro His Phe Ser Glu Thr Phe Pro Ser Leu Pro Ala Glu Gly Lys Val
225                 230                 235                 240

Tyr Ser Ser Asp Glu Glu Lys Leu Glu Pro Pro Ala Gly Asp Pro Ala
                245                 250                 255

Gly Ser Glu Gln Glu Glu Gly Ser Gly Asp Ser Glu Asp Ser
            260                 265                 270

Phe Leu Asp Ser Ser Ala Gly Gly Pro Gly Ala Leu Leu Gly Pro Lys
            275                 280                 285

Pro Lys Leu Lys Gly Ser Pro Gly Thr Gly Ala Glu Glu Gly Thr Pro
290                 295                 300

Val Ala Thr Gly Val Thr Thr Pro Gly Gly Lys Ser Arg Arg Arg Arg
305                 310                 315                 320

Thr Ala Phe Thr Ser Glu Gln Leu Leu Glu Leu Glu Lys Glu Phe His
                325                 330                 335

Cys Lys Lys Tyr Leu Ser Leu Thr Glu Arg Ser Gln Ile Ala His Ala
                340                 345                 350

Leu Lys Leu Ser Glu Val Gln Val Lys Ile Trp Phe Gln Asn Arg Arg
            355                 360                 365

Ala Lys Trp Lys Arg Ile Lys Ala Gly Asn Val Ser Ser Arg Ser Gly
            370                 375                 380

Glu Pro Val Arg Asn Pro Lys Ile Val Val Pro Ile Pro Val His Val
385                 390                 395                 400

Asn Arg Phe Ala Val Arg Ser Gln His Gln Gln Met Glu Gln Gly Ala
                405                 410                 415

Arg Pro

<210> SEQ ID NO 4
<211> LENGTH: 23
<212> TYPE: DNA
<213> ORGANISM: Artificial Sequence
<220> FEATURE:
<223> OTHER INFORMATION: Synthetic

<400> SEQUENCE: 4
ggaaccgctt cctccccaaa ttg                                          23

<210> SEQ ID NO 5
<211> LENGTH: 26
<212> TYPE: DNA
<213> ORGANISM: Artificial Sequence
<220> FEATURE:
<223> OTHER INFORMATION: Synthetic

<400> SEQUENCE: 5
tgctgtagtg gtcgaactgg ttcttc                                       26

<210> SEQ ID NO 6
<211> LENGTH: 24
<212> TYPE: DNA
<213> ORGANISM: Artificial Sequence
<220> FEATURE:
<223> OTHER INFORMATION: Synthetic

<400> SEQUENCE: 6
atcagcgtct actacaacga ggcc                                         24

<210> SEQ ID NO 7
<211> LENGTH: 32
```

```
<212> TYPE: DNA
<213> ORGANISM: Artificial Sequence
<220> FEATURE:
<223> OTHER INFORMATION: Synthetic

<400> SEQUENCE: 7
caaagatgaa attgtcaggc ctgaagagat gt                              32

<210> SEQ ID NO 8
<211> LENGTH: 30
<212> TYPE: DNA
<213> ORGANISM: Artificial Sequence
<220> FEATURE:
<223> OTHER INFORMATION: Synthetic

<400> SEQUENCE: 8
aagatggact tggtcaccta ctttggaaag                                 30

<210> SEQ ID NO 9
<211> LENGTH: 23
<212> TYPE: DNA
<213> ORGANISM: Artificial Sequence
<220> FEATURE:
<223> OTHER INFORMATION: Synthetic

<400> SEQUENCE: 9
cgtcttgggt gtcacaaaga ggg                                        23

<210> SEQ ID NO 10
<211> LENGTH: 19
<212> TYPE: DNA
<213> ORGANISM: Artificial Sequence
<220> FEATURE:
<223> OTHER INFORMATION: Synthetic

<400> SEQUENCE: 10
tgccgcctac tgagagcaa                                             19

<210> SEQ ID NO 11
<211> LENGTH: 21
<212> TYPE: DNA
<213> ORGANISM: Artificial Sequence
<220> FEATURE:
<223> OTHER INFORMATION: Synthetic

<400> SEQUENCE: 11
gtggcaggag tcaaggttgg t                                          21

<210> SEQ ID NO 12
<211> LENGTH: 30
<212> TYPE: DNA
<213> ORGANISM: Artificial Sequence
<220> FEATURE:
<223> OTHER INFORMATION: Synthetic

<400> SEQUENCE: 12
catgaagcaa tactatgggc tcttctcctc                                 30

<210> SEQ ID NO 13
<211> LENGTH: 29
<212> TYPE: DNA
<213> ORGANISM: Artificial Sequence
<220> FEATURE:
<223> OTHER INFORMATION: Synthetic

<400> SEQUENCE: 13
```
gacggcggaa attaatgaca acatccaag                                         29

<210> SEQ ID NO 14
<211> LENGTH: 25
<212> TYPE: DNA
<213> ORGANISM: Artificial Sequence
<220> FEATURE:
<223> OTHER INFORMATION: Synthetic

<400> SEQUENCE: 14
ccagaaaact ggggctcaag atctg                                             25

<210> SEQ ID NO 15
<211> LENGTH: 31
<212> TYPE: DNA
<213> ORGANISM: Artificial Sequence
<220> FEATURE:
<223> OTHER INFORMATION: Synthetic

<400> SEQUENCE: 15
gcaaacagat tagagaagtc agtctctgtg c                                      31

<210> SEQ ID NO 16
<211> LENGTH: 25
<212> TYPE: DNA
<213> ORGANISM: Artificial Sequence
<220> FEATURE:
<223> OTHER INFORMATION: Synthetic

<400> SEQUENCE: 16
gagcacaaga ggaagagaga gaccc                                             25

<210> SEQ ID NO 17
<211> LENGTH: 33
<212> TYPE: DNA
<213> ORGANISM: Artificial Sequence
<220> FEATURE:
<223> OTHER INFORMATION: Synthetic

<400> SEQUENCE: 17
gttgagcaca gggtacttta ttgatggtac atg                                    33

<210> SEQ ID NO 18
<211> LENGTH: 21
<212> TYPE: DNA
<213> ORGANISM: Artificial Sequence
<220> FEATURE:
<223> OTHER INFORMATION: Synthetic

<400> SEQUENCE: 18
gctggaagct gatgagctgc t                                                 21

<210> SEQ ID NO 19
<211> LENGTH: 28
<212> TYPE: DNA
<213> ORGANISM: Artificial Sequence
<220> FEATURE:
<223> OTHER INFORMATION: Synthetic

<400> SEQUENCE: 19
cttctcctca tctgagctgt acaccttc                                          28

<210> SEQ ID NO 20
<211> LENGTH: 27
<212> TYPE: DNA
<213> ORGANISM: Artificial Sequence
<220> FEATURE:
<223> OTHER INFORMATION: Synthetic

<400> SEQUENCE: 20
gaaaccccaa gattgttgtc cccatac                                          27

<210> SEQ ID NO 21
<211> LENGTH: 27
<212> TYPE: DNA
<213> ORGANISM: Artificial Sequence
<220> FEATURE:
<223> OTHER INFORMATION: Synthetic

<400> SEQUENCE: 21
cagatccctc gccttcctaa gttcttg                                          27

<210> SEQ ID NO 22
<211> LENGTH: 27
<212> TYPE: DNA
<213> ORGANISM: Artificial Sequence
<220> FEATURE:
<223> OTHER INFORMATION: Synthetic

<400> SEQUENCE: 22
ctggatctgg agaggaagat tgagtcg                                          27

<210> SEQ ID NO 23
<211> LENGTH: 26
<212> TYPE: DNA
<213> ORGANISM: Artificial Sequence
<220> FEATURE:
<223> OTHER INFORMATION: Synthetic

<400> SEQUENCE: 23
ctcatactgc gtgcggatct ctttca                                           26

<210> SEQ ID NO 24
<211> LENGTH: 32
<212> TYPE: DNA
<213> ORGANISM: Artificial Sequence
<220> FEATURE:
<223> OTHER INFORMATION: Synthetic

<400> SEQUENCE: 24
tgaaatgtgc ggagtgtaat cagtatttgg ac                                    32

<210> SEQ ID NO 25
<211> LENGTH: 24
<212> TYPE: DNA
<213> ORGANISM: Artificial Sequence
<220> FEATURE:
<223> OTHER INFORMATION: Synthetic

<400> SEQUENCE: 25
cacacagcgg aaacactcga tgtg                                             24

<210> SEQ ID NO 26
<211> LENGTH: 28
<212> TYPE: DNA
<213> ORGANISM: Artificial Sequence
<220> FEATURE:
<223> OTHER INFORMATION: Synthetic

<400> SEQUENCE: 26
gtttcagaat tgtagagcac gccacaag                                         28

<210> SEQ ID NO 27
<211> LENGTH: 26
<212> TYPE: DNA
<213> ORGANISM: Artificial Sequence
<220> FEATURE:
<223> OTHER INFORMATION: Synthetic

<400> SEQUENCE: 27
ctatgcagcg cagttaacat cgttcc                                          26

<210> SEQ ID NO 28
<211> LENGTH: 27
<212> TYPE: DNA
<213> ORGANISM: Artificial Sequence
<220> FEATURE:
<223> OTHER INFORMATION: Synthetic

<400> SEQUENCE: 28
gttaccccat tcaatgacac aactgcc                                         27

<210> SEQ ID NO 29
<211> LENGTH: 31
<212> TYPE: DNA
<213> ORGANISM: Artificial Sequence
<220> FEATURE:
<223> OTHER INFORMATION: Synthetic

<400> SEQUENCE: 29
cagcaaagtg atgttggaaa tgctttaggt g                                    31

<210> SEQ ID NO 30
<211> LENGTH: 25
<212> TYPE: DNA
<213> ORGANISM: Artificial Sequence
<220> FEATURE:
<223> OTHER INFORMATION: Synthetic

<400> SEQUENCE: 30
cacggctaca tcgagagtca ggtac                                           25

<210> SEQ ID NO 31
<211> LENGTH: 26
<212> TYPE: DNA
<213> ORGANISM: Artificial Sequence
<220> FEATURE:
<223> OTHER INFORMATION: Synthetic

<400> SEQUENCE: 31
caatctggct ccatttacct tctcac                                          26

<210> SEQ ID NO 32
<211> LENGTH: 21
<212> TYPE: DNA
<213> ORGANISM: Artificial Sequence
<220> FEATURE:
<223> OTHER INFORMATION: Synthetic

<400> SEQUENCE: 32
ctactgcaac ggcaacctgg g                                               21

<210> SEQ ID NO 33
<211> LENGTH: 20
<212> TYPE: DNA
<213> ORGANISM: Artificial Sequence
<220> FEATURE:
<223> OTHER INFORMATION: Synthetic

<400> SEQUENCE: 33
ccatgaagcg ggagatggcg                                          20

<210> SEQ ID NO 34
<211> LENGTH: 24
<212> TYPE: DNA
<213> ORGANISM: Artificial Sequence
<220> FEATURE:
<223> OTHER INFORMATION: Synthetic

<400> SEQUENCE: 34
caggctgtga ctgatgacca catc                                     24

<210> SEQ ID NO 35
<211> LENGTH: 27
<212> TYPE: DNA
<213> ORGANISM: Artificial Sequence
<220> FEATURE:
<223> OTHER INFORMATION: Synthetic

<400> SEQUENCE: 35
aggtcatgtt tggagatgac ccttgag                                  27

<210> SEQ ID NO 36
<211> LENGTH: 25
<212> TYPE: DNA
<213> ORGANISM: Artificial Sequence
<220> FEATURE:
<223> OTHER INFORMATION: Synthetic

<400> SEQUENCE: 36
ggagaaaaac tccacagcga cagtg                                    25

<210> SEQ ID NO 37
<211> LENGTH: 24
<212> TYPE: DNA
<213> ORGANISM: Artificial Sequence
<220> FEATURE:
<223> OTHER INFORMATION: Synthetic

<400> SEQUENCE: 37
agagccgttg agaagcttct ccac                                     24

<210> SEQ ID NO 38
<211> LENGTH: 25
<212> TYPE: DNA
<213> ORGANISM: Artificial Sequence
<220> FEATURE:
<223> OTHER INFORMATION: Synthetic

<400> SEQUENCE: 38
cagactccgt cagtttctgc agaag                                    25

<210> SEQ ID NO 39
<211> LENGTH: 25
<212> TYPE: DNA
<213> ORGANISM: Artificial Sequence
<220> FEATURE:
<223> OTHER INFORMATION: Synthetic

<400> SEQUENCE: 39
cttcaggttc cagggcatca ttctc                                    25

<210> SEQ ID NO 40

```
<211> LENGTH: 25
<212> TYPE: DNA
<213> ORGANISM: Artificial Sequence
<220> FEATURE:
<223> OTHER INFORMATION: Synthetic

<400> SEQUENCE: 40
gaggtctctg ttcaggtcaa cgtct                                          25

<210> SEQ ID NO 41
<211> LENGTH: 29
<212> TYPE: DNA
<213> ORGANISM: Artificial Sequence
<220> FEATURE:
<223> OTHER INFORMATION: Synthetic

<400> SEQUENCE: 41
ctcagtgaag atgaagctgg tctcattga                                      29

<210> SEQ ID NO 42
<211> LENGTH: 26
<212> TYPE: DNA
<213> ORGANISM: Artificial Sequence
<220> FEATURE:
<223> OTHER INFORMATION: Synthetic

<400> SEQUENCE: 42
agtgtcatca cctggtcacc aagttc                                         26

<210> SEQ ID NO 43
<211> LENGTH: 24
<212> TYPE: DNA
<213> ORGANISM: Artificial Sequence
<220> FEATURE:
<223> OTHER INFORMATION: Synthetic

<400> SEQUENCE: 43
cttcagcgtg gtgtagacct cctt                                           24

<210> SEQ ID NO 44
<211> LENGTH: 28
<212> TYPE: DNA
<213> ORGANISM: Artificial Sequence
<220> FEATURE:
<223> OTHER INFORMATION: Synthetic

<400> SEQUENCE: 44
gctacattgt cactcagatt ccaggagg                                       28

<210> SEQ ID NO 45
<211> LENGTH: 27
<212> TYPE: DNA
<213> ORGANISM: Artificial Sequence
<220> FEATURE:
<223> OTHER INFORMATION: Synthetic

<400> SEQUENCE: 45
atcctcacga agatgacaca gccatag                                        27
```